US006957107B2

(12) United States Patent
Rogers et al.

(10) Patent No.: US 6,957,107 B2
(45) Date of Patent: Oct. 18, 2005

(54) METHOD AND APPARATUS FOR MONITORING AND COMMUNICATING WITH AN IMPLANTED MEDICAL DEVICE

(75) Inventors: Bobby E. Rogers, San Diego, CA (US); Lon M. Severe, San Diego, CA (US); Philip N. Eggers, Poway, CA (US)

(73) Assignee: CardioNet, Inc., San Diego, CA (US)

( * ) Notice: Subject to any disclaimer, the term of this patent is extended or adjusted under 35 U.S.C. 154(b) by 323 days.

(21) Appl. No.: 10/099,929

(22) Filed: Mar. 13, 2002

(65) Prior Publication Data

US 2003/0172940 A1 Sep. 18, 2003

(51) Int. Cl.[7] .................................................. A61N 1/18
(52) U.S. Cl. ............................. 607/60; 607/30; 607/32; 128/904
(58) Field of Search ............................. 607/30, 32, 60; 128/903–904, 920

(56) References Cited

U.S. PATENT DOCUMENTS

| 3,478,344 A | 11/1969 | Schwitzgebel et al. ..... 340/312 |
| 3,768,014 A | 10/1973 | Smith et al. ............ 324/158 R |
| 3,885,552 A | 5/1975 | Kennedy ............... 128/2.05 R |
| 3,902,478 A | 9/1975 | Konopasek et al. ..... 128/2.06 F |
| 3,925,762 A | 12/1975 | Keitlinger et al. .......... 340/150 |
| 4,173,971 A | 11/1979 | Karz ........................... 128/702 |
| 4,183,354 A | 1/1980 | Sibley et al. ................ 128/711 |
| 4,211,237 A | 7/1980 | Nagel .......................... 128/698 |
| 4,230,127 A | 10/1980 | Larson ........................ 128/706 |
| 4,241,237 A | 12/1980 | Paraskevakos et al. .. 179/2 AM |
| 4,457,315 A | 7/1984 | Bennish ...................... 128/704 |
| 4,531,527 A | 7/1985 | Reinhold, Jr. et al. ...... 128/696 |
| 4,535,783 A | 8/1985 | Marangoni .................. 128/711 |
| 4,598,272 A | 7/1986 | Cox ............................ 340/539 |
| 4,651,157 A | 3/1987 | Gray et al. ................. 342/457 |
| 4,675,656 A | 6/1987 | Narcisse ..................... 340/539 |
| 4,706,689 A | 11/1987 | Man ............................ 128/903 |
| 4,742,357 A | 5/1988 | Rackley ...................... 342/457 |
| 4,750,197 A | 6/1988 | Denekamp et al. ........... 379/58 |
| 4,777,478 A | 10/1988 | Hirsch et al. ............... 340/573 |
| 4,785,291 A | 11/1988 | Hawthorne .................. 340/573 |
| 4,819,860 A | 4/1989 | Hargrove et al. ........... 228/668 |
| 4,886,064 A | * 12/1989 | Strandberg ................... 607/18 |
| 4,952,928 A | 8/1990 | Carroll et al. ......... 340/825.54 |
| 5,003,984 A | 4/1991 | Muraki et al. .............. 128/710 |
| 5,113,869 A | 5/1992 | Nappholz et al. ........... 128/696 |
| 5,172,698 A | 12/1992 | Stanko ........................ 128/697 |
| 5,223,844 A | 6/1993 | Mansell et al. ............. 342/357 |
| 5,301,105 A | 4/1994 | Cummings, Jr. ............ 364/401 |
| 5,309,920 A | 5/1994 | Gallant et al. .............. 128/710 |
| 5,311,197 A | 5/1994 | Sorden et al. .............. 342/457 |

(Continued)

FOREIGN PATENT DOCUMENTS

| DE | 4414 907 | 6/1995 | .......... F15B/15/14 |
| EP | 0 484 880 | 11/1991 | .......... G08B/25/10 |

(Continued)

Primary Examiner—Carl Layno
(74) Attorney, Agent, or Firm—Fish & Richardson P.C.

(57) ABSTRACT

A method and apparatus for communicating with and monitoring the operation of a device implanted within a patient. A transceiver capable of being implanted within a patient provides a communication interface between an implanted medical device and a monitor external to the patient's body. The external monitor can communicate with a remote monitoring center over a communication network. The external monitor also provides control signals to the implanted device via the transceiver unit. The transceiver apparatus is capable of two-way communication between the implanted device and the external monitor. The transceiver apparatus is also capable of detecting actions performed by the implanted device and physiological signals directly from the patient's body. Thus, the transceiver apparatus provides circuitry for determining whether an implanted medical device is operating properly. The transceiver apparatus provides a way to remotely reprogram one or more implanted medical devices.

19 Claims, 13 Drawing Sheets

U.S. PATENT DOCUMENTS

| | | | |
|---|---|---|---|
| 5,311,449 A | 5/1994 | Adams | 340/10.51 |
| 5,318,592 A | 6/1994 | Schaldach | 607/5 |
| 5,321,618 A | 6/1994 | Gessman | 364/413.06 |
| 5,334,974 A | 8/1994 | Simms et al. | 340/990 |
| 5,335,664 A | 8/1994 | Nagashima | 128/696 |
| 5,336,245 A | 8/1994 | Adams | 607/32 |
| 5,348,008 A | 9/1994 | Bornn et al. | 128/642 |
| 5,389,934 A | 2/1995 | Kass | 342/357 |
| 5,394,879 A | 3/1995 | Gorman | 128/707 |
| 5,418,537 A | 5/1995 | Bird | 342/356 |
| 5,422,816 A | 6/1995 | Sprague et al. | 364/449 |
| 5,423,869 A | 6/1995 | Poore | 607/18 |
| 5,458,123 A | 10/1995 | Unger | 128/696 |
| 5,461,365 A | 10/1995 | Schlager et al. | 340/573 |
| 5,470,233 A | 11/1995 | Fruchterman et al. | 434/112 |
| 5,479,482 A | 12/1995 | Grimes | 379/59 |
| 5,487,755 A | 1/1996 | Snell et al. | 607/27 |
| 5,497,149 A | 3/1996 | Fast | 340/988 |
| 5,503,158 A | 4/1996 | Coppock et al. | 128/696 |
| 5,504,491 A | 4/1996 | Chapman | 342/357 |
| 5,515,419 A | 5/1996 | Sheffer | 379/58 |
| 5,522,396 A | 6/1996 | Langer et al. | 128/696 |
| 5,544,661 A | 8/1996 | Davis et al. | 128/700 |
| 5,549,113 A | 8/1996 | Halleck et al. | 128/671 |
| 5,564,429 A | 10/1996 | Bornn et al. | 128/696 |
| 5,568,814 A | 10/1996 | Gallant et al. | 128/672 |
| 5,573,506 A | 11/1996 | Vasko | 604/65 |
| 5,576,952 A | 11/1996 | Stutman et al. | 364/413.02 |
| 5,579,775 A | 12/1996 | Dempsey et al. | 128/670 |
| 5,617,871 A | 4/1997 | Burrows | 128/696 |
| 5,620,472 A | 4/1997 | Rahbari | 607/27 |
| 5,626,624 A | 5/1997 | Schaldach et al. | 607/24 |
| 5,626,630 A | 5/1997 | Markowitz et al. | 607/60 |
| 5,629,678 A | 5/1997 | Gargano et al. | 340/573 |
| 5,649,303 A | 7/1997 | Hess et al. | 455/63 |
| 5,652,570 A | 7/1997 | Lepkofker | 340/573 |
| 5,678,562 A | 10/1997 | Sellers | 128/710 |
| 5,704,351 A | 1/1998 | Mortara et al. | 128/630 |
| 5,704,364 A | 1/1998 | Saltzstein et al. | 128/696 |
| 5,704,366 A | 1/1998 | Tacklind et al. | 128/716 |
| 5,713,856 A | 2/1998 | Eggers et al. | 604/65 |
| 5,720,770 A | 2/1998 | Nappholz et al. | 607/30 |
| 5,720,771 A | 2/1998 | Snell | 607/60 |
| 5,724,025 A | 3/1998 | Tavori | 340/573 |
| 5,729,197 A | 3/1998 | Cash | 340/539 |
| 5,730,143 A | 3/1998 | Schwarzberg | 128/710 |
| 5,731,757 A | 3/1998 | Layson, Jr. | 340/573 |
| 5,748,103 A | 5/1998 | Flach et al. | 340/870.07 |
| 5,749,367 A | 5/1998 | Gamlyn et al. | 128/696 |
| 5,749,907 A | 5/1998 | Mann | 607/27 |
| 5,752,976 A | 5/1998 | Duffin et al. | 607/32 |
| 5,759,199 A | 6/1998 | Snell et al. | 607/60 |
| 5,882,300 A | 3/1999 | Malinouskas et al. | 600/300 |
| 5,891,169 A | 4/1999 | Boheim et al. | 607/4 |
| 5,913,827 A | 6/1999 | Gorman | 600/509 |
| 5,913,881 A | 6/1999 | Benz et al. | 607/36 |
| 5,931,791 A | 8/1999 | Saltzstein et al. | 600/513 |
| 5,941,829 A | 8/1999 | Saltzstein et al. | 600/509 |
| 5,944,659 A | 8/1999 | Flach et al. | 600/300 |
| 5,950,110 A | 9/1999 | Hendrickson | 455/1 |
| 5,959,529 A | 9/1999 | Kail, IV | 340/539 |
| 5,964,794 A | 10/1999 | Bolz et al. | 607/121 |
| 5,966,692 A | 10/1999 | Langer et al. | 705/3 |
| 5,970,986 A | 10/1999 | Bolz et al. | 128/899 |
| 5,987,352 A | 11/1999 | Klein et al. | 600/509 |
| 5,987,519 A | 11/1999 | Peifer et al. | 709/230 |
| 6,026,008 A | 2/2000 | Feese | 365/63 |
| 6,038,469 A | 3/2000 | Karlsson et al. | 600/512 |
| 6,073,046 A | 6/2000 | Patel et al. | 600/509 |
| 6,083,248 A | 7/2000 | Thompson | 607/30 |
| 6,088,608 A | 7/2000 | Schulman et al. | 600/345 |
| 6,093,146 A | 7/2000 | Filangeri | 600/300 |
| 6,101,478 A | 8/2000 | Brown | 705/2 |
| 6,102,856 A | 8/2000 | Groff et al. | 600/301 |
| 6,154,674 A | 11/2000 | Meier | 607/23 |
| 6,160,478 A | 12/2000 | Jacobsen | 340/539 |
| 6,181,966 B1 | 1/2001 | Nigram | 607/4 |
| 6,192,274 B1 | 2/2001 | Worzewski | 607/14 |
| 6,225,901 B1 | 5/2001 | Kail, IV | 340/539 |
| 6,245,092 B1 | 6/2001 | Schaldach | 607/1 |
| 6,263,243 B1 | 7/2001 | Lang | 607/17 |
| 6,466,793 B1 | 10/2002 | Wallstedt et al. | 455/450 |
| 6,497,655 B1 * | 12/2002 | Linberg et al. | 600/300 |
| 6,564,104 B2 * | 5/2003 | Nelson et al. | 607/60 |
| 6,622,050 B2 * | 9/2003 | Thompson | 607/60 |
| 6,695,885 B2 * | 2/2004 | Schulman et al. | 623/25 |
| 6,804,558 B2 * | 10/2004 | Haller et al. | 607/30 |
| 2002/0143576 A1 | 10/2002 | Nolvak et al. | 705/2 |
| 2003/0032991 A1 * | 2/2003 | Poore | 607/32 |
| 2003/0144711 A1 * | 7/2003 | Pless et al. | 607/60 |

FOREIGN PATENT DOCUMENTS

| | | | |
|---|---|---|---|
| EP | 0 834 846 | 1/1996 | G08B/25/10 |
| EP | 0 811 959 | 6/1997 | G08B/25/10 |
| EP | 1 022 035 A1 | 7/2000 | A61N/1/372 |
| EP | 1 072 994 | 1/2001 | G06F/19/00 |
| FR | 2 787 905 | 12/1998 | G08B/25/10 |
| WO | WO 94/13197 | 6/1994 | A61B/5/00 |
| WO | WO 96/25877 | 8/1996 | A61B/5/0404 |
| WO | WO 97/00708 | 1/1997 | A61N/1/372 |
| WO | WO 99/44494 | 9/1999 | A61B/5/00 |
| WO | WO 00/30529 | 6/2000 | A61B/5/00 |
| WO | WO 00/62663 | 10/2000 | A61B/5/00 |

\* cited by examiner

SURVEILLANCE MODE

METHOD AND APPARATUS FOR MONITORING AND COMMUNICATING WITH AN IMPLANTED MEDICAL DEVICE

FIELD OF THE INVENTION

The invention relates to communication systems used to monitor medical devices implanted in a living being. More particularly, the invention relates to a transceiver device which facilitates the remote monitoring and reprogramming of one or more implanted medical devices within a patient.

BACKGROUND OF THE INVENTION

Patients that have been identified as having a chronic physical condition, such as a cardiac disorder, are managed in a variety of ways. For some, devices such as a pacemaker or a cardiac defibrillator may be implanted into their body. Implantable medical devices ("IMDs") may be designed to perform a variety of functions. These functions include stimulation of body organs, drug delivery, and simple monitoring of physiological conditions of a patient. Most IMDs operate independently of any external inputs; but occasionally the devices need to be recharged, reprogrammed, or otherwise checked to ensure proper performance. Typically, a communication interface is provided between the IMD and an external monitor to reprogram and monitor the IMD. Unfortunately, such communication interfaces are very short-range due to the limited size and power allowances of the IMD. Additionally, in most cases today, recharging of the IMD device is an invasive procedure which creates trauma for the patient. To accomplish recharging, the IMD is removed, recharged, and replaced in a surgical procedure after a predetermined time or when the battery charge level is deemed "low."

Due to the short-range communication limitation, activities such as monitoring, maintenance, and programming of an IMD must be performed using equipment in close proximity to the IMD. Typically, such monitoring and maintenance requires an IMD patient to visit a physician's office where the physician can communicate with the IMD by opening a low frequency communication channel. Once the channel is open, the physician can reprogram the IMD, conduct a performance check, and perform any other diagnostic functions deemed necessary. Although this form of IMD interface communication has worked well, there is a need to bring IMD patients into a more efficient and less restrictive communication paradigm. It is cumbersome, time-consuming, and costly for patients to visit a physician's office to have an IMD reprogrammed. It is also cumbersome and costly to conduct and/or schedule transtelephonic pacer checks, which require application of a magnetic field at the patient's skin over the area where the IMD is located.

Furthermore, in the event an implanted cardiac defibrillator discharges, it is extremely important that a record of the event is captured and a physician is notified almost immediately. Prior solutions to the need of physician notification include devices that would notify a physician when the patient manually triggered the notification process. However, if a patient had a heart-attack, stroke, or other debilitating event, the patient may not be able to trigger the communication device, and a doctor would not be notified. Thus, it is desired to provide a means of remote and continuous monitoring of a patient's IMD performance without requiring patient-initiated surveillance of the IMD.

Longer range communication systems have been proposed to be implemented within the IMDs themselves. In U.S. Pat. No. 6,083,248, Thompson discloses a system in which a transceiver is incorporated within the IMD. This system provides a long-range communication system that enables remote monitoring of the IMD. The transceiver communicates with an external patient communication control device that is worn by the patient, or otherwise located in close proximity. The external control device is linked with a remote medical support network. This system is further described in U.S. Pat. No. 5,752,976 to Duffin & Thompson.

One problem with the use of a transceiver within an IMD, as described in the above-referenced patents, is that it does not address the needs of patients having older IMDs that do not incorporate such a transceiver. Another problem with the transceiver being located within the MD itself is the increased size of the IMD, making the IMD unsuitable in some applications. Additionally, a high powered transceiver may interfere with the operation of the IMD if located within the IMD. Thus, the IMD becomes a more complicated device, leading to an increased failure rate, which is unacceptable in life-threatening situations.

Another problem encountered when the transceiver is incorporated within the IMD is there is no way to verify that the IMD is operating properly. Specifically, there is no verifiable way to ascertain whether or not the IMD is accurately sensing the patient's actual condition as intended by the physician who programmed the IMD. There is also no verifiable way to determine whether the IMD is responding to the physiological conditions to which it was designed to respond. Put another way, there is no verifiable way to ascertain whether the IMD is performing like it "thinks" it is.

In U.S. Pat. No. 5,626,630 Markowitz describes a transceiver that can be adapted for use with new and old IMD's; however this transceiver must be electrically connected to the IMD. This fact makes this solution unworkable for patients with preexisting implants because it would require the removal and rewiring of the IMD. In addition, if a patient who currently has an IMD wired to an implanted transceiver, as described by Markowitz, needs to have a second IMD implanted, the surgical procedure is further complicated by the need to physically wire the already-implanted transceiver to the new IMD.

Further to the disclosure of the patents discussed above, remote two-way communication is also possible with implantable devices by utilizing the system described in Kail U.S. Pat. No. 5,959,529. The Kail Patent enables communication from an ambulatory subject to a monitoring center. However, the system described by Kail does not provide for communication with, monitoring, and programming an MD within a patient.

Thus there is a need to enable communication with IMDs that will not require a visit to a physician's office and will not necessarily require any pre-scheduling. There is also a need to provide a means for more constant monitoring of an IMD while allowing the patient to be mobile and free. Specifically, there is a need to monitor, periodically or continuously, the performance of an IMD within a patient to determine whether the IMD is operating as intended without inhibiting the patient's mobility or freedom. In the event the IMD is not operating properly, or a patient is in an emergency condition, there is a need for automatic physician notification. It is also desired to provide a transceiver that can monitor and otherwise communicate with multiple IMDs in a patient without being electrically connected to the IMD. In addition, there is a need to provide a transceiver that is capable of communicating with old, pre-existing IMDs as well as newly implanted IMDs.

SUMMARY OF THE INVENTION

In order to communicate remotely and at will with a previously-implanted IMD, and/or with an IMD to be implanted in the future, a transceiver apparatus is implanted into a patient to provide a communication interface between the IMD and an external monitor, which in turn communicates with a monitoring center. The monitoring center then notifies a physician in response to the communication received from the external monitor if necessary. The implanted transceiver is hermetically sealed and remains electrically isolated from the IMD with which it is intended to communicate. The implantable transceiver can be free-floating within the body or be affixed to the IMD. The transceiver is designed to communicate with pre-existing and new IMDs as appropriate. The transceiver design is selected based on size, power requirements, and so forth, depending on the communication requirements of the devices it will be monitoring and with which it will be communicating.

One embodiment of the invention provides an implantable transceiver device electronically isolated from and in communication with one or more medical devices implanted within a patient. In another embodiment, the invention provides a communications system capable of continuously or periodically monitoring the performance of a medical device implanted within a patient without substantially limiting the patient's mobility. In a further embodiment, the invention enables the remote programming of a device implanted within a patient without requiring the patient to visit a physician's office or otherwise pre-schedule a reprogramming session.

The advantages of the invention over the prior art are realized in a first aspect of the invention which is a transceiver apparatus for use in conjunction with a device implanted into a living being and an external monitor. The transceiver comprises a communication system for communicating with the implanted device and the external monitor, a memory for storing digital information, a control system for executing instructions stored in the memory and managing communication over the communication system, and a power supply that provides power to the communication system, the control system, and the memory.

The purposes of the invention are further accomplished in another aspect of the invention which is an implantable transceiver apparatus that monitors a device implanted into a living being, and provides a communication interface with an external monitor. The transceiver comprises at least one two-way transceiver for communicating with the external monitor and/or the implanted device and at least one sensor for detecting stimulus generated by the implanted device and/or the living being. The transceiver also comprises a memory for storing digital information and a control system for executing instructions stored in the memory and managing communication using at least one two-way transceiver and managing stimulus detection using at least one sensor. The transceiver further comprises a power supply that provides power to at least one of the two-way transceivers, at least one of the sensors, the control system, and the memory, and a hermetically-sealed case suitable for implantation in the living being, the case housing at least one of the two-way transceivers, at least one of the sensors, the control system, and the memory.

The implantable transceiver operates to monitor and communicate with various types of implantable devices and sensors. Some examples include, but are not limited to, artificial replacement organs (pacemaker, etc.), defibrillators, transplanted organs with sensors placed upon them, pumps (insulin, etc.), blood chemistry and activity meters, accelerometers, and devices to monitor and assist pregnancy, ovulation, EEG, ECG, sleep, respiration, blood pressure, blood gases, glucose levels and so forth. For definitional purposes herein, all such devices are referred to as IMDs. In one embodiment, the implantable transceiver includes one or more sensors. These sensors allow the implantable transceiver to sense the activity of the IMD as well as sensing physiological data directly from the patient. For example, one sensor may detect an electrical impulse discharged by an implanted defibrillator, while another sensor may detect ECG signals directly from the patient. In this way, the invention provides a way to determine whether an IMD is operating properly by comparing physiological data sensed by the implantable transceiver with physiological data sensed by the IMD. Furthermore, the implantable transceiver is capable of determining whether the IMD is properly responding to the physiological condition of the patient.

One advantage of the invention is that the transceiver is capable of automatically sending an alert message to the monitoring center, and ultimately a physician, if the physiological signals from the patients body indicate the patient is in need of immediate medical attention. In this way the invention fulfills the need of automatic physician notification without patient-initiated communication.

Another advantage of the invention is, with the transceiver apparatus electrically isolated from the IMD, a physician can simply implant a transceiver apparatus into a patient with an already-implanted IMD, rather than replace the existing IMD with a new IMD incorporating an integrated transceiver. In this way, surgery is simplified and the impact of the surgery on the patient is minimized.

An additional advantage of the invention is that the transceiver apparatus is capable of monitoring and communicating with more than one IMD. Thus, a patient with multiple IMDs could have a single transceiver implanted that will facilitate the reprogramming, monitoring, and recharging of each individual IMD. This reduces the number of devices implanted into a patient as well as the size and complexity of the IMDs. The invention also eliminates any need to electrically connect an already-implanted transceiver with a soon-to-be-implanted IMD, thereby reducing the time and physical impact of surgery. In addition, companies that design IMDs can design all new IMDs to be compatible with a standard and separate transceiver. Thus, with standardized technology, the cost to patients is decreased and IMD options are increased with increased compatibility.

In one embodiment, the implantable transceiver operates in various modes. In one mode the implantable transceiver monitors the operation of the IMD and detects situations in which the IMD is not functioning properly. In the event an IMD is not functioning properly, the implantable transceiver reprograms the IMD according to reprogramming instruction received from the monitoring center or already recorded in the memory of the implantable transceiver. In another mode, the implantable transceiver monitors the patient's physical condition and automatically notifies a physician when an emergency condition is detected.

DETAILED DESCRIPTION OF THE INVENTION

Figure 1:
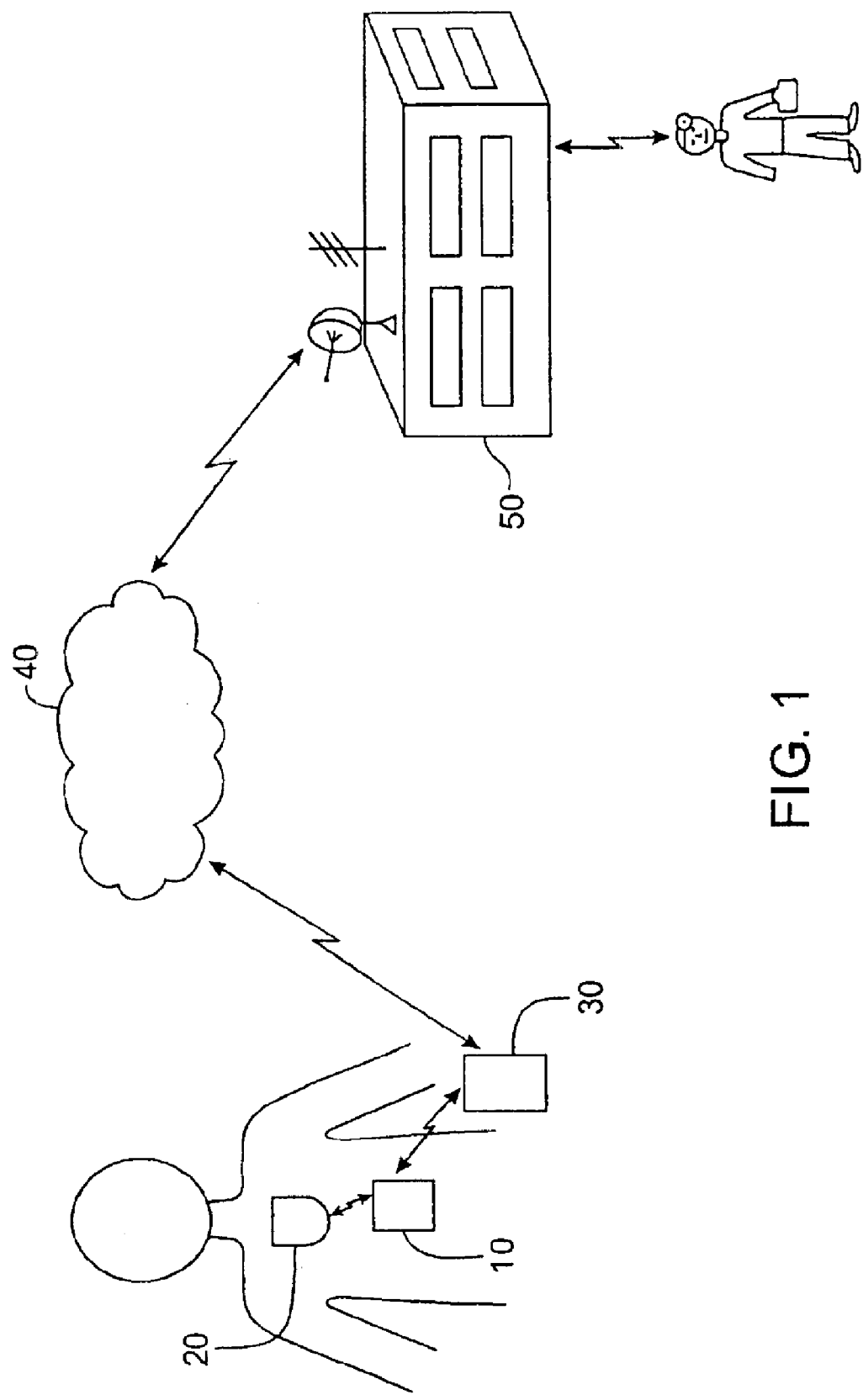
FIG. 1 is a conceptual diagram illustrating the communication system facilitated by the invention.

FIG. 1 illustrates one embodiment of the communication paradigm facilitated by the invention. An implantable transceiver 10 is implanted within a patient's body in close proximity, and so as to and communicate in both directions with, an IMD 20. The implantable transceiver 10 may be physically attached to the IMD 20 or it may be free-floating in the patient's body. The implantable transceiver 10 may otherwise be attached to the patient's body as well. For example, the implantable transceiver 10 may not be implanted within the patient's body, but rather be taped or otherwise secured to the outside of the patients body in close proximity to the IMD 20 within the patient's body. In some embodiments, the implantable transceiver 10 can be mechanically attached to the MD 20, while still using a transceiver to communicate with the IMD 20 and remaining electronically independent. The term "electronically independent" refers to the absence of hard electrical connections and does not exclude the use of wireless interfacing.

The implantable transceiver 10 also communicates in both directions with an external monitor 30. The external monitor 30 can be a mobile or hand held apparatus. For example, the external monitor 30 can be similar to a personal digital assistant (PDA). A PDA is a common mobile device well known in the art. The external monitor 30 can include a display that allows graphics and text to be viewed by the patient or physician. A touch panel can also be utilized. In one embodiment, the external monitor displays information in sufficient detail for diagnosing the patient. The number of attributes displayed on the display may be limited by the design parameters of the external monitor 30. For example, a product, manufactured by CardioNet, a California Corporation, of San Diego, Calif., referred to as "The Monitor," could be used as the external monitor. The CardioNet monitor contains a 32 bit microprocessor with 64 megabytes of Flash memory. This allows up to 24 hours of Sensor data to be stored and analyzed. The monitor also contains a cell phone modem which allows the device to communicate with the monitoring center when the patient is mobile. A built in GPS unit allows patient location to be determined. When the Monitor is placed into its charging base, the monitor can contact the monitoring center through a land line modem. Alternatively, the external monitor 30 may be any similar device capable of two-way communication with the implantable transceiver 10.

The external monitor 30 utilizes a communication network 40, which may be a land-line telephone network, a wireless network, a satellite communication network, or other suitable network to facilitate two-way communication with a monitoring center 50. In one embodiment, the monitoring center 50 is a remotely located medical support network comprising medical staff, communication systems, data processing and storage systems, and tracking systems able to remotely monitor the operation of the implantable transceiver 10 within the patient. For example, the monitoring center 50 may be located in a room within a hospital or local doctor's office. The monitoring center 50 may also be an independent structure. Hospital staff, including nurses, physicians, and technical support, operate and watch the tracking, communication, and processing systems that are in communication with the external monitor 30. In one embodiment, the monitoring center 50 operates automatically and independently, notifying medical personnel when a pre-determined set of circumstances is detected by the implantable transceiver 10 and communicated to the monitoring center 50. Notification of medical personnel may be done by e-mail, telephone, pager, cell phone, or other suitable communication device. In this way, the monitoring center 50 requests and receives information about the IMD 20 and the condition of the patient and alerts a physician if necessary. Thus, communication may flow in both directions between the monitoring center 50 and the implantable transceiver 10 through the external monitor 30 and the communication network 40.

In one embodiment, the monitoring center 50 has means to send and receive communication to and from the implantable transceiver 10. For example, some embodiments of the invention comprise a monitoring center 50 with wireless-digital communication systems able to send and receive data to and from the implantable transceiver 10. Other communication examples include land-line communications, satellite communications, and analog wireless communications.

The monitoring center 50 also has means to store data received from the implantable transceiver 10. Further, the monitoring center has means to process and execute commands and instructions in accordance with the received data. In some embodiments, the monitoring center 50 has commercially available computer units with memory modules and processors capable of processing data received from the implantable transceiver. Any microprocessor or other processor capable of executing instructions in accordance with the data received from the implantable transceiver 10 will fulfill this aspect of the invention. Additionally, any memory module capable of storing the data received will fulfill this aspect of the invention.

In some embodiments, if the implantable transceiver 10 sends information indicating the IMD 20 needs to be reprogrammed, the monitoring center 50 has means to notify pertinent medical staff that reprogramming is needed. For example, in some embodiments, the monitoring center 50 uses a computer network to send a notification via e-mail to one or more physicians or other medical staff. The network can be a local intranet or the Internet or other suitable computer network capable of facilitating the sending and receiving of e-mail messages. In some embodiments, the notification is sent using telephone lines, either wired or wireless. These notifications may be sent to a pager or telephone of the medical personnel. After a doctor or other relevant medical personnel receives the notification, the party receiving the notification may then determine whether any action, such as reprogramming the IMD 20 or patient emergency assistance, is required.

In another example, the monitoring center 50 can automatically compile reprogramming instructions and send those instructions to the implantable transceiver 10 without alerting medical personnel. In this embodiment, the processing means in the monitoring center 50 analyze the data received from the implantable transceiver 10 and compile reprogramming instructions based on the performance of the IMD 20 as indicated by the received data. In a further example, the implantable transceiver 10 can automatically compile and implement instructions to reprogram the IMD 20 without communications to or from the monitoring center 50.

Figure 2:
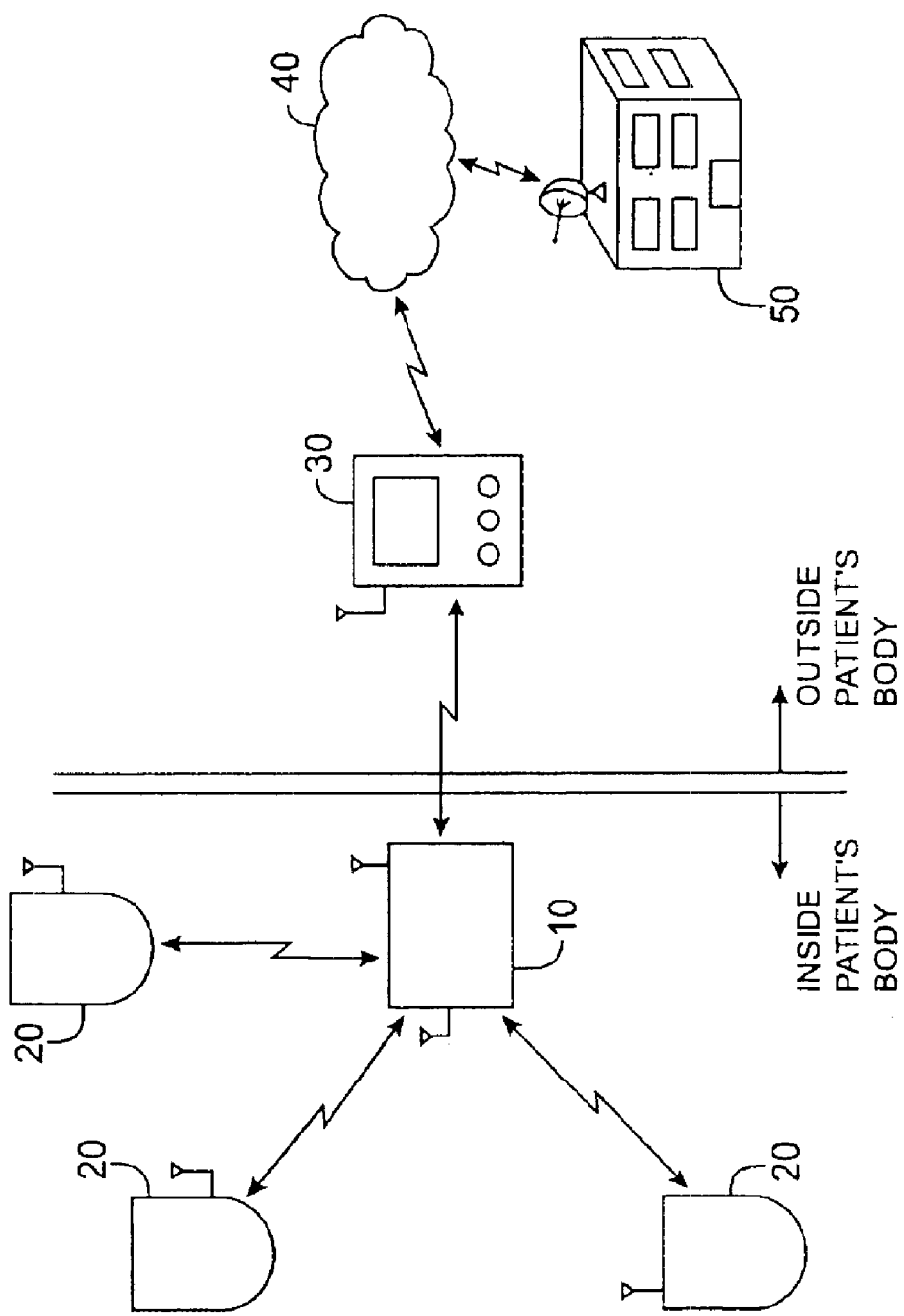
FIG. 2 is a diagram further illustrating an embodiment of the communication system facilitated by the invention.

FIG. 2 illustrates an embodiment of the communication system implemented by the invention described above with reference to FIG. 1, wherein the implantable transceiver 10 may be used to communicate with multiple IMDs 20 within a patient. For example, the implantable transceiver 10 may facilitate communication between a monitoring center 50 and an implanted defibrillator as well as an implanted insulin pump. The implantable transceiver 10 may also facilitate communication with various other types of IMDs 20. Such IMDs 20 include, but are not limited to, artificial replacement organs (pacemaker, etc.), defibrillators, transplanted organs with sensors placed upon them, pumps (insulin, etc.), blood chemistry and activity meters, accelerometers, and devices to monitor and assist pregnancy, ovulation, EEG, ECG, sleep, respiration, blood pressure, blood gases, glucose levels and so forth. In addition, the implantable transceiver 10 may be included within an IMD 20.

In one example of the invention, the implantable transceiver 10 sends and receives messages to both an implanted insulin pump and an implanted defibrillator. In addition, the implantable transceiver 10 sends and receives messages to and from the external monitor 30, which can be worn or carried by the patient, or otherwise be kept in sufficient proximity to the implantable transceiver 10 to allow communication. The external monitor 30 may then communicate with the monitoring center 50 as described above with reference to FIG. 1.

In another embodiment of the invention, the implantable transceiver 10 utilizes Global Positioning System (GPS) technology and satellite communications to communicate the location of the patient to the external monitor 30, and ultimately to the monitoring center 50. Alternatively, the external monitor 30 includes the GPS technology to ascertain the patient's location, if the patient is wearing or otherwise carrying the external monitor 30, or if the external monitor 30 is in close proximity to the patient. The patient's location is sent to the monitoring center 50 as described above, and ultimately to a physician if necessary. In some embodiments, the patients location can also be determined utilizing a relative positioning system, ascertaining the patient's location in relation to some known object or location.

In one embodiment of the invention, the implantable transceiver 10 is used to reprogram an IMD 20 from a remote location, such as a monitoring center 50. This is further discussed below with reference to FIGS. 7 and 7A.

In another embodiment, the implantable transceiver 10 continuously monitors the performance of the IMD 20 in order to ascertain when such reprogramming is necessary. This embodiment is further discussed below with reference to FIG. 6A.

Figure 2A:
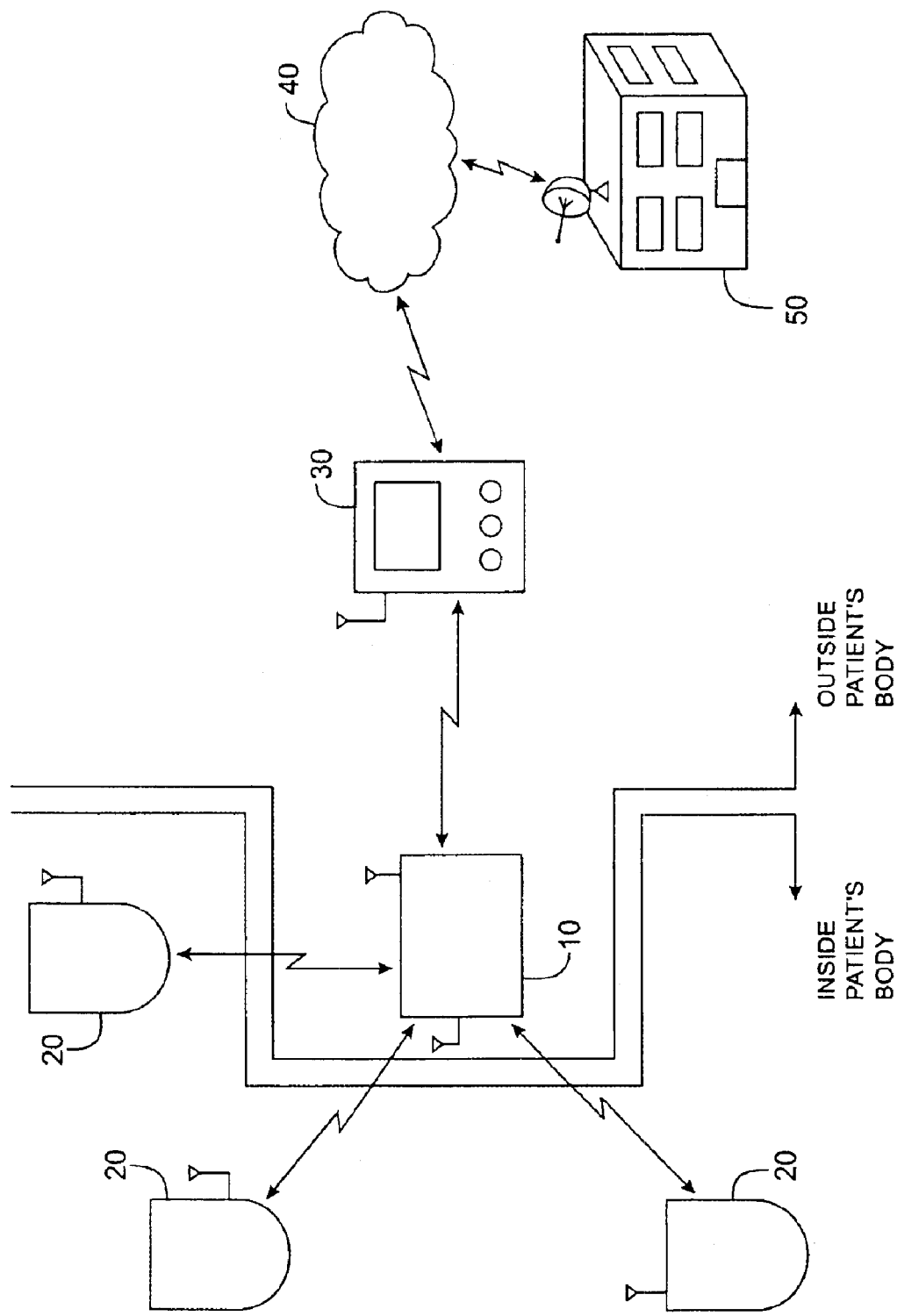
FIG. 2A is a diagram illustrating an embodiment of the communication system that locates the implantable transceiver external to the patient.
Figure 3:
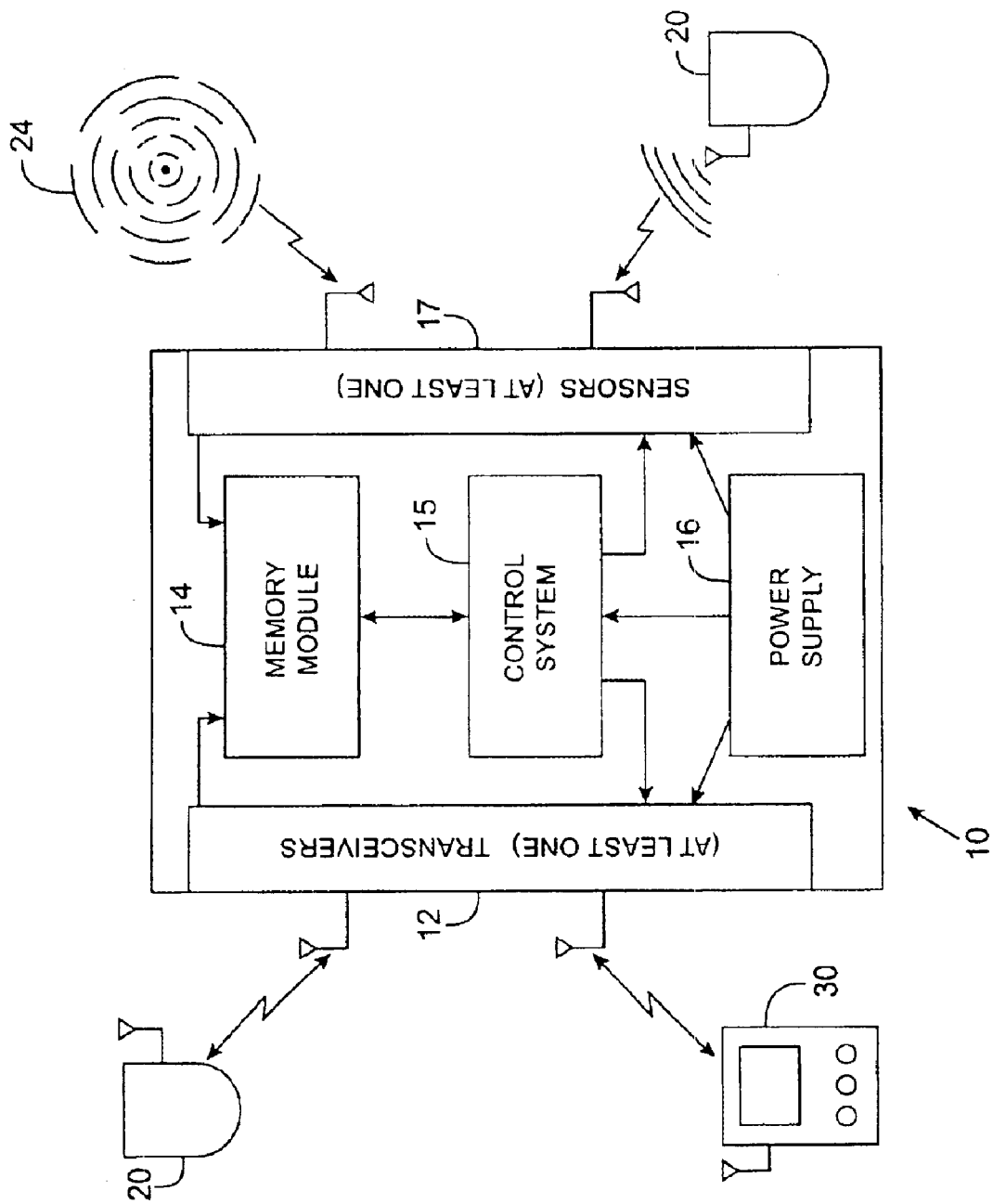
FIG. 3 is a block diagram showing the various components that may be included in an implantable transceiver unit.

FIG. 2A is a diagram illustrating an embodiment of the communication system that locates the transceiver 10 external to the patient. As illustrated in FIG. 2A, the transceiver 10 may be worn externally. For example, the transceiver 10 may be taped onto the body at a location that is proximate to the IMD 20, and as described above, it can provide communication between the IMD 20 and the external monitor 30. In such an application, the case that houses the transceiver 10 may be designed specifically to be worn external to the patient. FIG. 3 illustrates various components that may be included in one embodiment of the implantable transceiver 10, along with the functions performed by each. One aspect of the invention is to provide a transceiver apparatus 10 for use with an IMD 20 implanted into a living being and an external monitor 30. The transceiver apparatus 10 comprises a communication system 12 to facilitate communication with the IMD 20 and the external monitor 30, a memory device 14 for storing digital information, a control system 15 for executing instructions stored in the memory device 14 and managing the communication system 12, and a power supply 16 to provide power to all aspects of the transceiver apparatus 10. The transceiver apparatus 10 can further include at least one or more sensor units 17 configured to sense physiological conditions of the patient. In one embodiment, the communication system of the implantable transceiver 10 includes at least one two-way transceiver unit 12 to facilitate wireless communication with the IMD 20 and the external monitor 30. Known wireless techniques include personal area networks (PAN) and local area networks (LAN). Examples of these wireless techniques include Bluetooth technology and technology based on an IEEE 802.11b wireless specification. Separate transceiver units 12 may be used to communicate with one or more IMDs 20 and the external monitor 30. Each of the two-way transceiver units 12 may request and receive information from both the IMD 20 and the external monitor 30. For example, physiological data may be obtained through communication with the IMD 20. This data represents what physiological conditions the IMD 20 is sensing. In other words, the implantable transceiver 10 receives data indicating what the IMD 20 "thinks" the patient's physical condition is.

The implantable transceiver 10 also includes a memory device 14 which stores data and information received through communication with the IMD 20 and the external monitor 30. The memory device 14 may be populated by read-only-memory ("ROM") and/or random-access-memory ("RAM") devices depending on the design requirements. For example, it may be desirable to have system level software stored in a ROM format because these types of programs are seldom changed. Many types of ROMs are known in the art, including, programmable read-only memory ("PROM"), erasable programmable read-only memory ("EPROM"), electrical read-only memory ("EEPROM"), and flash-EEPROM. The most common type of ROM is masked read-only memory, which is typically programmed by a manufacturer. This type of memory does not permit subsequent re-programming of the memory device 14. PROM is similar to ROM except that PROM is typically programmed after manufacture. For example, a medical professional could program the PROM after receiving the transceiver 10.

EPROM does allow multiple programming of the memory device 14 by utilizing ultraviolet ("UV") light to erase the memory. EEPROM permits its erasure with the use of electricity. A more recent type of ROM is called flash-ROM which further decreases the erasure time as this memory device 14 is erased completely since it lacks the circuitry of the EEPROM for allowing partial erasure of individual locations. Flash-ROM does allow information to be written to an erased location even though some other locations were already written to after the memory was completely erased.

RAM may also be used for the memory device 14. RAM allows the memory device 14 to be written to and read from, and will maintain its contents until power is interrupted to the memory device 14. Examples of RAM include static random-access memory ("SRAM") and dynamic random-access memory ("DRAM"). One or more of these types of ROM and/or RAM may be used in further embodiments of the invention depending on the design requirements. The prior descriptions are not intended to limit the types of memory devices 14 known in the art that could be used in the invention. The memory device 14 can have sufficient capacity to store reprogramming instructions, monitoring thresholds, and communication time schedules. In general, the memory device 14 has sufficient capacity in the form of ROM and/or RAM to store any information needed for accurate and reliable monitoring of the IMD 20.

For example, in one embodiment the memory device 14 may store a data report of the actions performed by the IMD 20 with respect to the patient's physical condition at the time of those actions. The data report can include the physiologic conditions of the patient as sensed by one or more sensor units 17 of the implantable transceiver 10, described below, and as sensed by the IMD 20 and communicated to the implantable transceiver 10. In this way, the memory device 14 stores data necessary to determine if the IMD 20 is sensing the actual physiologic conditions of the patient, and responding accordingly. In other words, the data stored in the memory device 14 is used to determine whether the IMD 20 is operating as it "thinks" it is.

In some embodiments, the implantable transceiver 10 may include one or more sensor units 17. A sensor unit 17 can be used to sense an action performed by the IMD 20. For example, the IMD action can be represented by an electronic impulse from an implanted defibrillator or a discharge of insulin from an insulin pump. One of skill in the art will recognize that there are many well known functions performed by various IMDs 20, and the examples given herein are not meant to limit the scope of the invention. Data representative of the IMD action can then be stored in the memory device 14 and can also be sent to the external monitor 30 through a two-way transceiver unit 12.

In one embodiment, one or more sensor units 17 may be used to sense patient condition signals 24. For example, the patient condition signals 24 may be blood gases, glucose levels, respiration, ECG signals, etc. Data representing the patient condition signals 24 is collected directly from the patient's body through the sensor unit 17 independent of the activity of the IMD 20. The data representing the patient condition signals 24 can then be stored in the memory device 14 and can also be transmitted to the external monitor 30 through a two-way transceiver unit 12.

The implantable transceiver 10 also includes a control system 15 which organizes and manages the activities of the sensor units 17, the two-way transceiver units 14, and the memory device 14. The control system 15 may include a processor. For example, a programmable logic device, microprocessor, and microcontroller could be used as known to those of ordinary skill in the art. In one embodiment, the control system 15 is selected from an Atmel (San Jose, Calif.) AVR family of microcontrollers which includes an AVR MEGA 103. Alternatively, the control system 15 can include a FPGA or ASIC, which are configured to perform certain tasks. However, the control system 15 need only comprise any system that is capable of controlling the communication activities and data collection of the implantable transceiver 10. The control system 15 may process data representing patient condition signals 24 obtained through one or more sensor units 17 so as to compare that data with the data representing patient condition signals 24 obtained through the IMD 20 and communicated to the implantable transceiver 10.

In one embodiment, the implantable transceiver 10 can be programmed to send an alert message to the monitoring center 50 if the above-described data comparison shows that the data received through the sensor units 17 is not consistent with the data being obtained through the IMD 20. In this way, the implantable transceiver 10 provides a way to determine whether the IMD 20 is functioning properly. Furthermore, the control system 15 can execute reprogramming instructions previously stored in the memory device 14 automatically if the data comparison indicates the IMD 20 is not operating as desired.

The implantable transceiver 10 also has a power source 16. The power source 16 allows the implantable transceiver 10 to be self-powered and may, in some embodiments, be recharged by induction or other means not requiring surgical removal. For example, the implantable transceiver 10 can be powered by stored electromechanical energy similar to a watch that stores energy generated by human movement.

In embodiments where the transceiver 10 is located external to the patient, as illustrated in FIG. 2A, the external transceiver 10 can also include one or more sensor units 17 for sensing stimuli generated by the DAD and/or the patient as described above.

Figure 4:
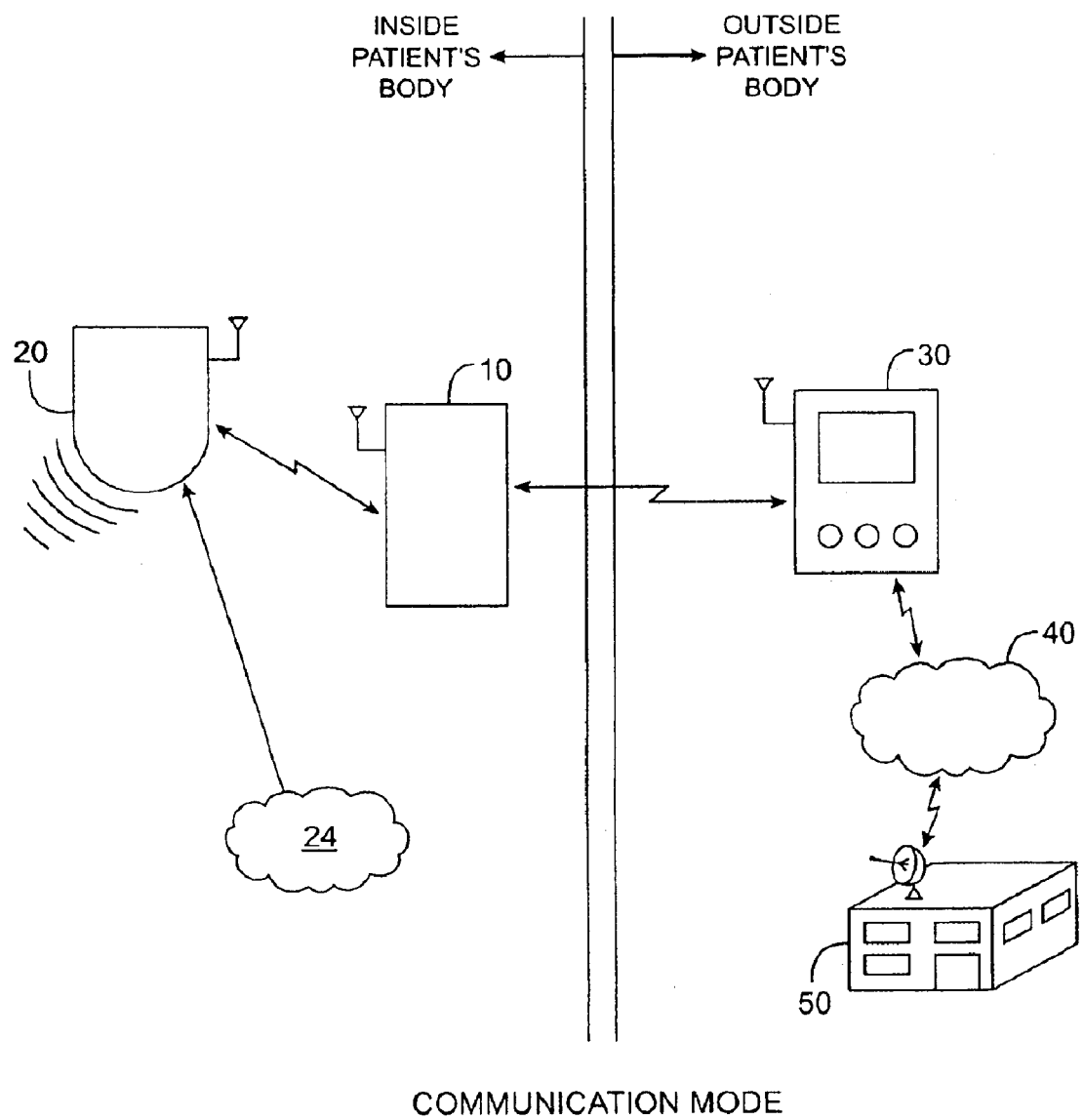
FIG. 4 is a block diagram showing an implantable transceiver unit operating in an active communication mode with an IMD and an external monitor.

FIG. 4 illustrates the implantable transceiver 10 operating in an active communication mode. In some situations, an IMD 20 is programmed to perform an IMD action in response to certain patient condition signals 24 of the patient, which are detected by the IMD 20. The implantable transceiver 10 can receive data from the IMD 20 concerning the IMD actions 22 and the patient condition signals 24 sensed by the IMD 20 that triggered those IMD actions 22.

For example, the IMD 20 may be an implanted cardiac device (i.e. a pacemaker or defibrillator), which monitors ECG signals it collects from the heart. When previously specified conditions are met, the IMD 20 discharges an electronic impulse to pulse or defibrillate the heart. The implantable transceiver 10 may communicate with the IMD 20 and receive data concerning the discharge of the IMD 20, the patient's current status, and the patient's physical condition which triggered the discharge as sensed by the IMD 20. This data, including the patient's physical location (using GPS technology, for example), is then sent to the external monitor 30, which in turn may send the data across the communication network 40 to the monitoring center 50. Alternatively, the GPS technology is located in the external monitor 30. In some embodiments, the monitoring center 50 has a database containing medical personnel contact information, which may include medical staff and physician names, telephone numbers, pager numbers, e-mail addresses, work schedules, and other information useful in contacting a physician. The monitoring center 50 can contact a physician or take other action as necessary. The monitoring center 50 may also return a communication to the IMD 20, such as reprogramming instructions according to the method described with reference to FIG. 7 below.

In an alternative embodiment, the implantable transceiver 10 automatically executes reprogramming instructions if the data indicates the IMD 20 did not operate properly, such as not discharging properly or in a timely manner. In this way, the need for medical personnel intervention and assistance is minimized and the patients ambulatory ability is maximized.

Figure 5:
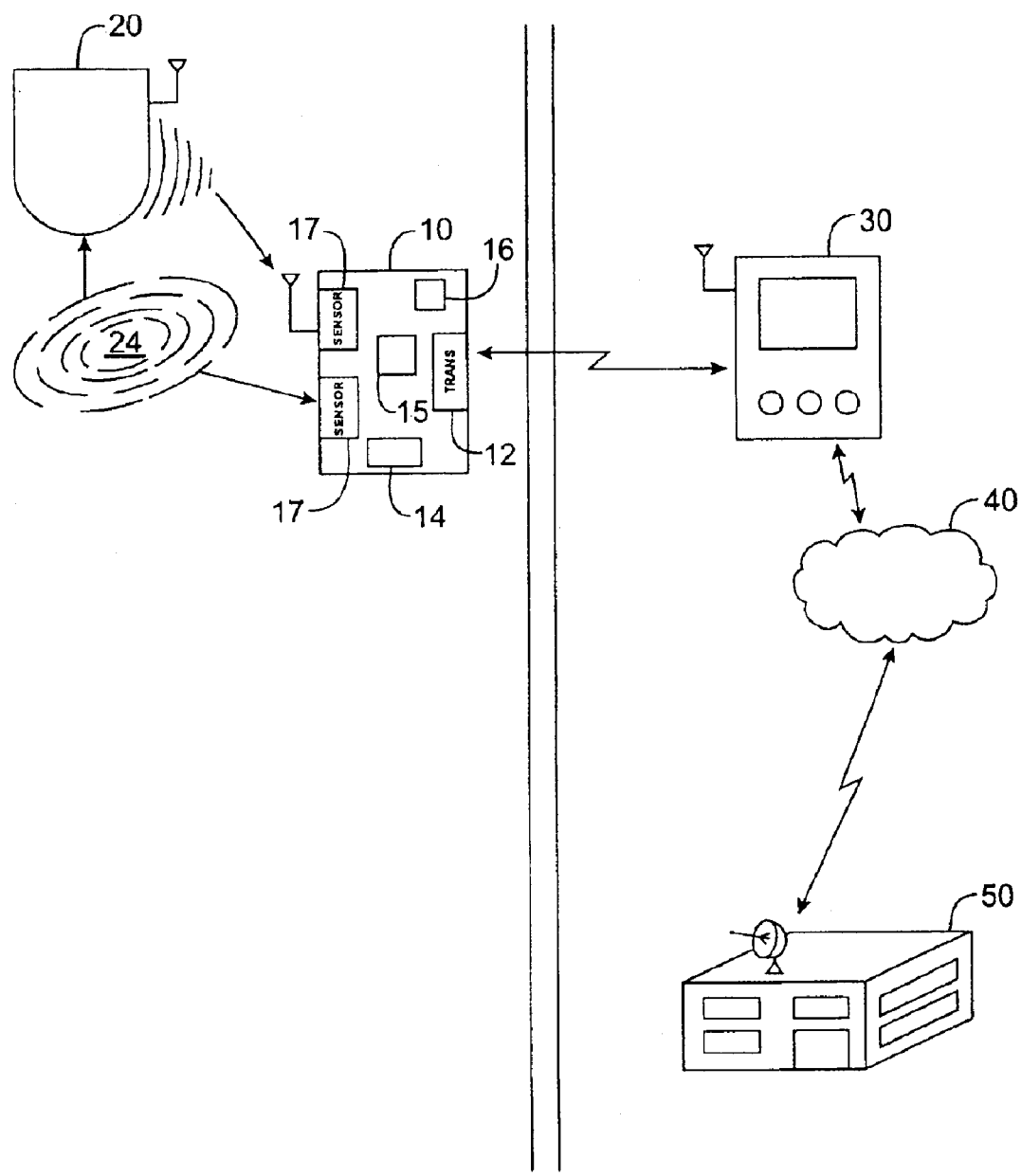
FIG. 5 is a block diagram showing an implantable transceiver unit operating in a surveillance mode with an IMD.

FIG. 5 illustrates the implantable transceiver 10 operating in an external observer role referred to as a "surveillance mode." In this mode, the implantable transceiver 10 receives data through one or more sensor units 17. The sensor units 17 detect the IMD actions 22 as well as the patient condition signals 24 from the patient. While operating in this surveillance mode, the invention fulfills many valuable purposes, such as determining if the performance of the IMD 20, as perceived by the IMD 20 itself, matches reality. In other words, surveillance mode operation provides a way for the implantable transceiver 10 to determine whether the IMD 20 is performing the proper IMD action in accordance with the proper patient condition signals 24. For example, the performance of the IMD could be monitored according to the system of FIG. 3 and the methods described in reference to FIGS. 5 and 6A below.

Data received through the sensor units 17 is stored in the memory device 14 of the implantable transceiver 10 and may be sent to the external monitor 30. The external monitor 30 may then send the data to the monitoring center 50, where response action may or may not be taken. In another embodiment, the control system 15 of the implantable transceiver 10 processes the data obtained through the sensor units 17 and executes reprogramming instructions as necessary.

The actions of the implantable transceiver 10 while operating in a surveillance mode may be done with or without patient knowledge. For example, the patient can be notified by a physician or other medical staff that the IMD 20 will need reprogramming. Alternatively, reprogramming instructions may be sent to the IMD 20 via the implantable transceiver 10 without patient knowledge or notification.

For example, if the data received by the monitoring center 50 from the implantable transceiver 10 indicates the IMD 20 is not operating properly, the monitoring center 50 sends reprogramming instructions back to the IMD 20. Alternatively, if the data sensed and received by the implantable transceiver 10 indicates the IMD 20 is operating in accordance with certain predetermined conditions, the implantable transceiver 10 automatically implements reprogramming instructions already stored on the memory device 14, which are designed to correct such a predetermined condition of operation.

In one embodiment, the implantable transceiver 10 communicates with the IMD 20 when one of the following three events occurs: a) interrogation in accordance with a pre-defined schedule; b) when an external signal is received from the external monitor 30 or the monitoring center 50; or c) when the implantable transceiver 10 observes a predetermined change within the body, such as an ECG arrhythmia. In each case the implantable transceiver 10 then opens a communication channel with the IMD 20 to request information. It is also possible in some embodiments that the IMD 20 could initiate a request for communication with the implantable transceiver 10.

In addition, if a sensor unit 17 has been provided on the implantable transceiver 10 and the sensor unit 17 detects some IMD action, then the implantable transceiver 10 may open a communication channel with the IMD 20 and send a report of the sensed IMD action to the external monitor 30. In still other embodiment, the implantable transceiver 10 may have prescheduled times at which it periodically opens up a communication channel with the IMD 20 and then reports back to the external monitor 30. Otherwise, the implantable transceiver may remain in an "inactive" watching state.

In some embodiments, a periodic interrogation of the implantable transceiver 10 may be programmed into the external monitor 30. For example, at periodic intervals (e.g. every five minutes) the external monitor 30 may send a request to the implantable transceiver 10 to open a communication channel and provide a report of the patient's condition and/or the performance of the IMD 20. It should be apparent that the request for interrogation may originate from any number of sources, such as the external monitor 30, the monitoring center 50, or manually by a physician or health care professional via an interface such as a keyboard that is connected to the monitoring center 50.

The implantable transceiver 10 in this embodiment could also be contained within the MD 20, external to the IMD 20 as stated before, or electrically connected but external thereto. Another variant does not necessarily require an implantable transceiver 10 and uses the external monitor 30 to pick up signals from an IMD 20. In this case, the methods to activate communication are the same as before. One difference is that the user is required to place the external monitor 30 in close proximity to the IMD 20 before communication channels can function properly.

Figure 6:
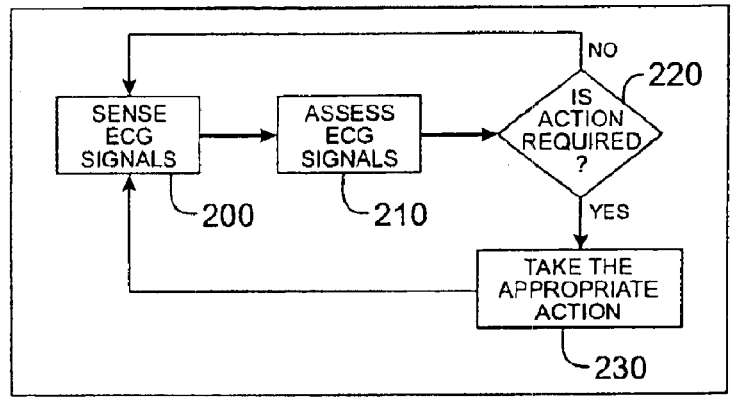
FIG. 6 is a flowchart illustrating a typical method of operation of an IMD within a patient.

FIG. 6 is a flow chart illustrating a typical operation of an MD 20 represented by an implanted cardiac device, such as a defibrillator or pacemaker. In step 200, the IMD 20 senses the ECG signals in the patient's body. Next, in step 210, the MD 20 assesses the ECG signals. Moving to step 220, the IMD 20 determines whether the ECG signals indicate that action is required. If the ECG signals indicate that an action from the IMD 20 is needed, the process proceeds to step 230, and the IMD 20 takes an appropriate action, such as discharging an appropriate level of electrical stimulus into the patient's body. Typically, the IMD 20 is, preprogrammed to take action when it senses a pre-determined patient condition represented by the ECG signals. The process then returns to step 200, where the IMD 20 again senses the ECG signals from the patient and functions as described above. If it is determined in step 220 that no action from the MD 20 is needed, the process returns to step 200 and continues to function as described above.

Figure 6A:
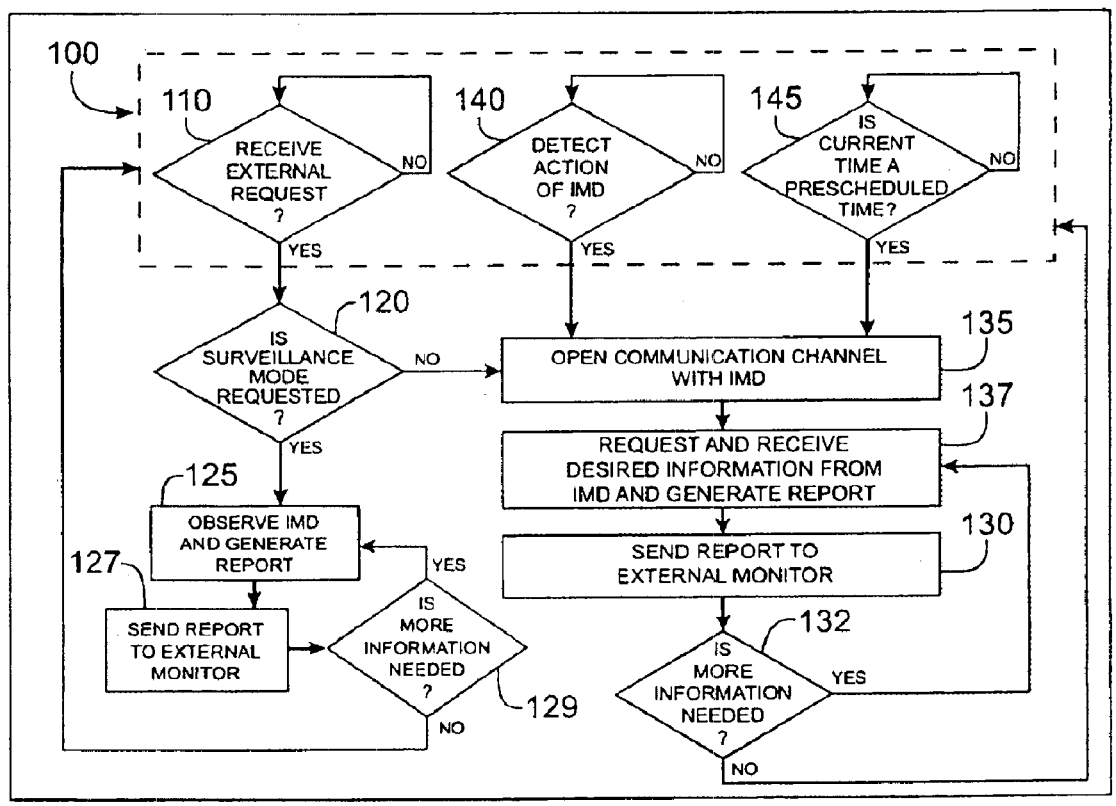
FIG. 6A is a flowchart illustrating some operation modes of the implantable transceiver.

FIG. 6A is a flow chart illustrating the operation of the implantable transceiver 10 in both a surveillance mode and an active communication mode. In one embodiment, the implantable transceiver 10 initially operates in an inactive watching state 100. In this state, the implantable transceiver 10 does not communicate with or actively monitor the patient or the IMD 20. Active monitoring or surveillance refers to sensing the actions of the IMD 20 as well as the physiological signal of the patient and recording the sensed data. In one embodiment, any one of three events may cause the implantable transceiver 10 to leave the inactive watching state 100 and actively monitor or communicate with the IMD 20. In other words, one of three events causes the implantable transceiver to enter an active surveillance mode as described above with reference to FIG. 5, or an active communication mode as described with reference to FIG. 4 above. These three events are described below with reference to steps 110, 140 and 145.

In step 110, if an external request is received by the implantable transceiver 10, the process leaves the inactive watching state 100 and moves to step 120. Such an external request may originate from the external monitor 30, the monitoring center 50, or the IMD 20 itself. The external request may either direct the implantable transceiver 10 to enter a surveillance mode or an active communication mode. If the implantable transceiver 10 does not receive an external request, the implantable transceiver 10 remains in the inactive watching state 100.

In step 120, if the external request received is a request for surveillance mode, the process moves to step 125, and the implantable transceiver 10 actively monitors the actions of the MD 20 and/or the physiological status of the patient as described above with reference to FIG. 5. The implantable transceiver 10 generates a report of the obtained data concerning the activity of the IMD 20 and the patient's physical condition, which is stored in the memory device 14 of the implantable transceiver 10.

Next, in step 127, the implantable transceiver 10 sends the data report to the external monitor 30 and the process moves to step 129. If, in step 129, it is determined that no more data or information is needed from the implantable transceiver 10, the process returns to the inactive watching state 100 to await further triggering events as described with reference to steps 110, 140, and 145. In some embodiments, such a determination is made after a predetermined period of time or after communication is received from the monitoring center 50 which indicates no more information is needed. Alternatively, if it is determined that more data or information is needed from the implantable transceiver 10 in step 129, the process returns to step 125 and proceeds as described above.

Referring again to step 120, if surveillance mode is not requested, the external source requests an active communication mode and the process proceeds to step 135, wherein the implantable transceiver 10 opens communication channels with the IMD 20 and the external monitor 30. Next, in step 137, the implantable transceiver 10 communicates with the IMD 20 to request the needed information according to the external source request. During step 137, the implantable transceiver 10 can also obtain data regarding patient condition and IMD performance through one or more sensor units 17.

Moving to step 130, the implantable transceiver 10 sends a report of the needed information to the external monitor 30. The needed information may include data such as what action was taken by the IMD 20 and when such action was taken; the patient's physical condition just prior to the action of the IMD 20; the patient's physical location (GPS data); and the patient's current physical condition. Additionally, while operating in an active communication mode, the implantable transceiver 10 can execute previously stored instructions to reprogram the IMD 20 if necessary. After step 130, the process moves to step 132. If, in step 132, it is determined that no more data or information is needed from the implantable transceiver 10, the process returns to the inactive watching state 100 to await further triggering events as described with reference to steps 110, 140, and 145. In some embodiments, such a determination is made after a predetermined period of time or after communication is received from the monitoring center 50 which indicates no more information is needed. Alternatively, if it is determined that more data or information is needed from the implantable transceiver 10 in step 132, the process returns to step 137 and proceeds as described above.

The process can also leave the inactive watching state 100 if an action performed by the IMD 20 is detected by the implantable transceiver 10 in step 140. If, at step 140, the implantable transceiver 10 detects an action taken by the IMD 20, as described above with reference to step 230 in FIG. 6, the process proceeds to step 135 and continues as described above. If, at step 140, the implantable transceiver 10 does not detect an action taken by the MD 20, as described above with reference to step 230 in FIG. 6, the process returns to the inactive watching state 100 to await further triggering events as described with reference to steps 110, 140, and 145.

The process can also leave an inactive watching state 100 if, in step 145, the current time is a prescheduled time wherein the implantable transceiver is programmed to enter an active communication mode, as described above with reference to FIG. 4. At step 145, if the current time is such a pre-scheduled time, the process proceeds to step 135 and continues as described above. If, at step 145, the current time is not such a pre-scheduled time, the process then returns to the inactive watching state 100 to await further triggering events as described with reference to steps 110, 140, and 145.

The processes illustrated by FIGS. 6 and 6A show that the implantable transceiver 10, external to the IMD, can communicate in various manners. For example, in the context of a pacemaker, the implantable transceiver 10 will first receive an external signal generated by the external monitor 30 originating from the external monitor 30 or the monitoring center 50. This external signal tells the implantable transceiver 10 to open a communication channel with the pacemaker. Once communications are open, the implantable transceiver 10 can conduct a two-way dialog with the pacemaker to obtain performance data and to issue new instructions. Alternatively, or simultaneously, the implantable transceiver 10 can monitor the pacemaker's performance in a surveillance mode. The surveillance mode can be activated by an external signal or can be done continuously. If done continuously, triggering parameters may be established to tell the implantable transceiver 10 when it should actively transmit data externally. In this surveillance mode it is not necessary to have open communications with the pacemaker.

In a similar fashion the implantable transceiver 10 can interact with implanted cardiac defibrillators. One notable situation of such interaction would be detection of an event within the surveillance mode, as described above with reference to FIGS. 5, 6, and 6A, when the defibrillator discharges into the patient. One or more sensor units 17 detect this large voltage change. In response, the implantable transceiver 10 then quickly seeks to open a communication channel with the implanted defibrillator. The implantable transceiver 10 will then ask for information from the implanted defibrillator regarding the current patient status, the status of the defibrillator device, the status (or readings) of the patient just prior to discharge and any other relevant information i.e. time, date, patient location etc. This information is sent to the external monitor 30 once collected or while being collected. The external monitor 30 then relays this information over the communication network 40 to the monitoring center 50 and ultimately to the physician. In this way, the implantable transceiver 10 performs a valuable function connecting patients with physicians without costly office visits and enables better management and control of IMDs 20.

In some embodiments, the active communication mode and the surveillance mode may be used simultaneously or cooperatively. For example, an event sensed during the surveillance mode may trigger the implantable transceiver 10 to open an active communication link with the IMD 20. In this way, referring again to FIG. 6A, an event detected during step 125 may cause the implantable transceiver 10 to open communication with the IMD 20 according to step 135 as described above.

Figure 7:
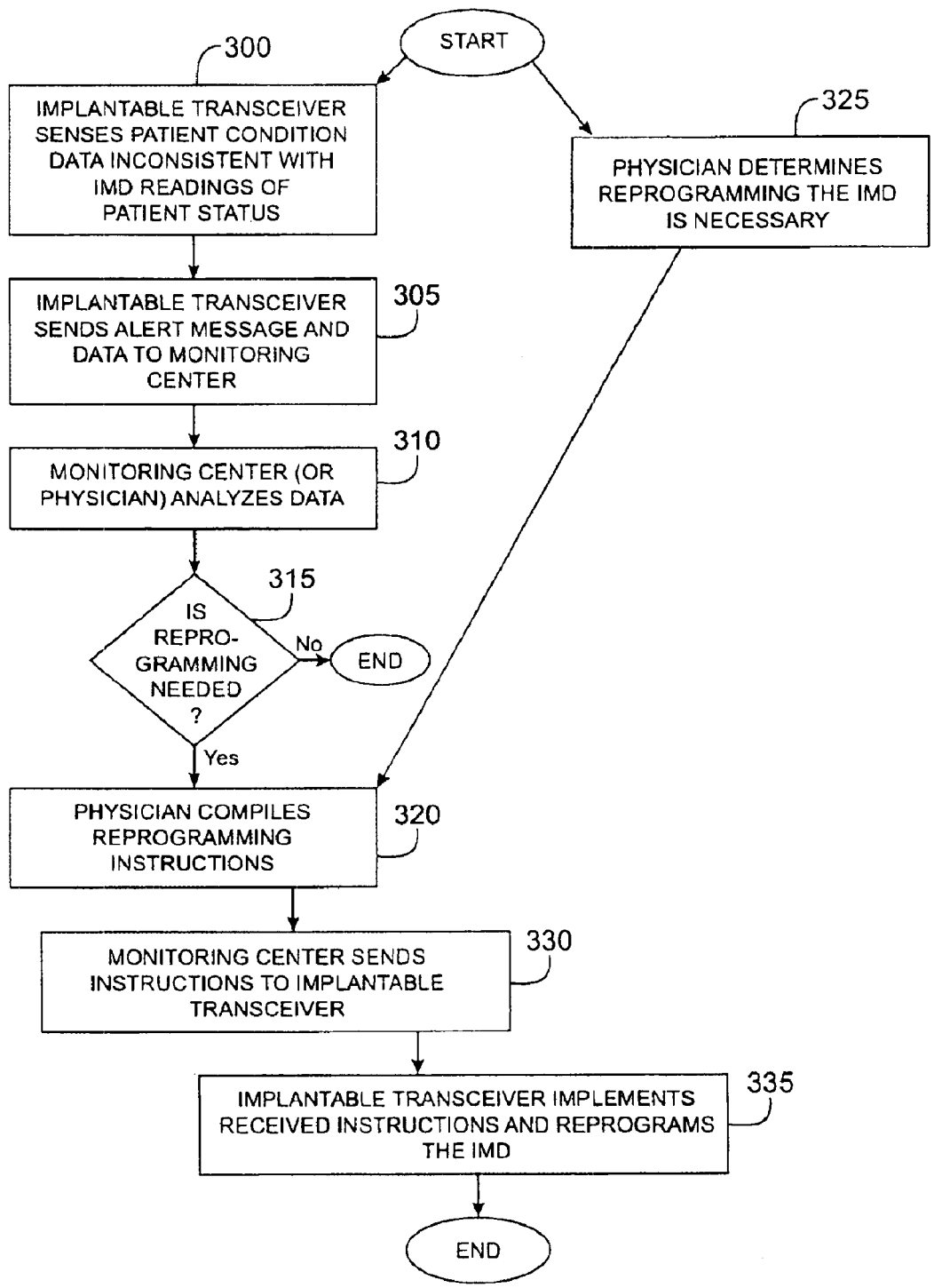
FIG. 7 is a flowchart illustrating a process of remotely reprogramming an IMD using the implantable transceiver.

FIG. 7 is a flowchart illustrating one method of reprogramming the IMD 20 using the implantable transceiver 10. In one embodiment, the process of reprogramming the IMD 20 may be triggered by either the implantable transceiver 10, or by a physician. In the case where the process is initiated by the implantable transceiver 10, the process begins at step 300, wherein the implantable transceiver 10 senses physiological data, such as ECG signals, from the patient inconsistent with the physiologic signals being sensed by the IMD 20. Next, at step 305, the implantable transceiver 10 sends an alert message containing the IMD 20 performance data to the monitoring center 50. The alert message may contain data showing the IMD 20 is not functioning properly. The alert message is sent through the external monitor 30 and the communication network 40 as described above. Moving to step 310, the monitoring center 50 receives the alert message and data, and a physician or the monitoring center 50 analyzes the data. In step 315, the monitoring center 50, a physician, or other medical personnel determines whether the IMD 20 needs to be reprogrammed. If the IMD 20 needs to be reprogrammed, the process moves to a step 320, as will be described below. If, in step 315, reprogramming is not necessary, the process ends and will begin again when triggered by the event described above in step 300, or by the event described below in step 325.

In the case where the process is triggered by a user, such as a physician, the process begins at step 325, wherein the physician determines reprogramming is necessary. Such a determination may be made for a variety of reasons. For example, the physician may determine during an office visit or after a phone consultation that the patient's needs have changed. The process then proceeds directly to step 320, wherein the physician compiles reprogramming instructions. Regardless of how the process begins, the process proceeds from the step 320 to step 330, where the monitoring center 50 sends the reprogramming instructions to the implantable transceiver through the communication network 40 and the external monitor 30. Finally, at step 335, the implantable transceiver 10 receives the reprogramming instructions and implements them to reprogram the IMD 20.

Figure 7A:
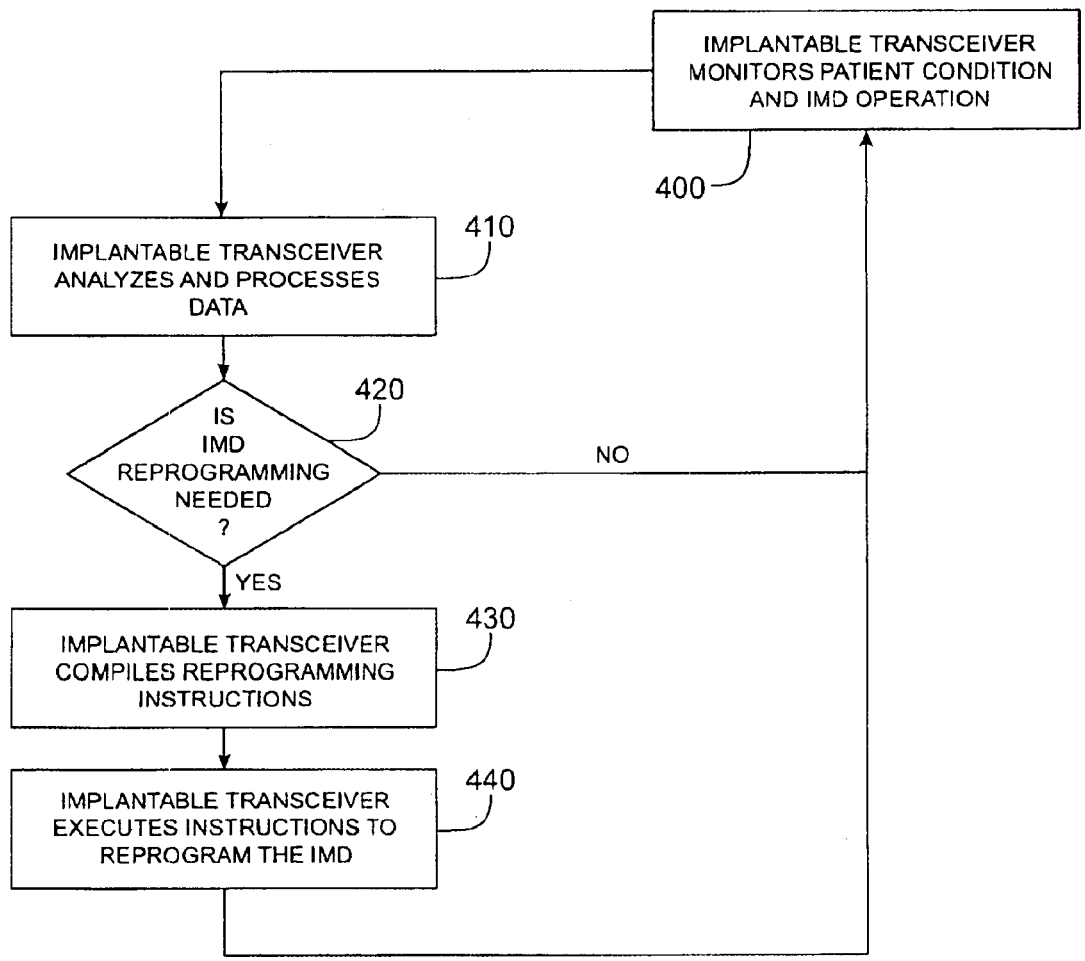
FIG. 7A is a flowchart illustrating a process of automatic reprogramming of an IMD using the implantable transceiver.

FIG. 7A is a flowchart showing an alternative method of reprogramming the IMD 20 using only the implantable transceiver 10. Initially, in step 400, the implantable transceiver is operating in an active surveillance mode, monitoring the condition of the patient and/or the operation of the IMD 20 as described above with reference to FIG. 6A. Next, in step 410, the implantable transceiver 10 analyzes or processes the data obtained while monitoring the patient and the IMD 20. This processing step is carried out by the control system 15. If, in step 420, the results of processing the data indicate reprogramming the IMD 20 is needed, the process moves to step 430. For example, if the data indicates the IMD 20 performed an action, such as discharging an electrical pulse, when the patient's condition did not warrant such an action, the IMD 20 will need to be reprogrammed to ensure proper operation in the future. In another example, the data may indicate the IMD 20 senses a particular physical condition from the patient, such as low blood pressure, while the implantable transceiver 10 senses an inconsistent condition, such as high blood pressure. In such a case, the MD 20 may not be operating properly and may need reprogramming.

In step 430, after reprogramming has been deemed necessary in step 420, the implantable transceiver 10 compiles instructions to reprogram the IMD 20 according to the indications of the data analyzed in step 410. The instructions are compiled using information previously stored in the memory device 14, such as reprogramming software. Once the reprogramming instructions are compiled, the instructions are executed by the control system 15 to reprogram the IMD 20 in step 440. The process then returns to step 400 where the implantable transceiver 10 monitors the patient and the IMD 20.

Figure 8:
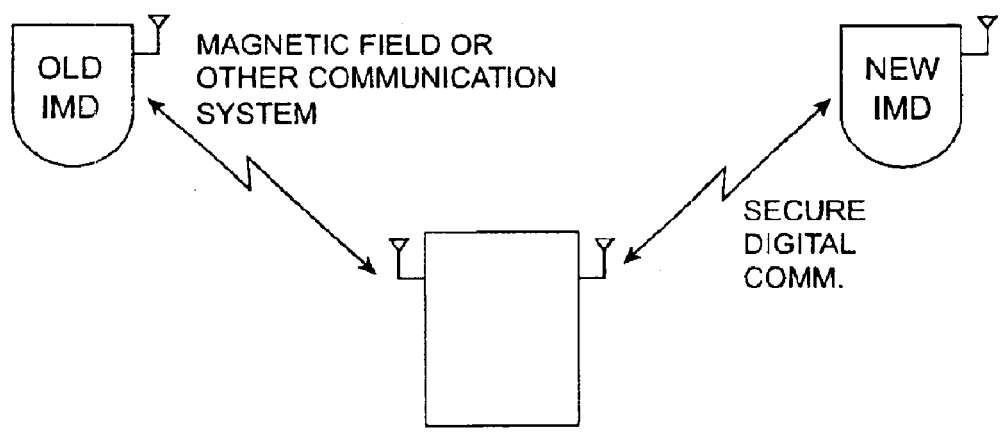
FIG. 8 is a block diagram showing the implantable transceiver of the invention, which is capable of communicating with old and new IMDs having different communication systems.

FIG. 8 illustrates the implantable transceiver 10 used in communicating with and monitoring old and new IMDs 20. For example, some old IMDs 20 require a magnetic field communication system, while newer IMDs 20 are capable of secure digital communication. In some embodiments, the implantable transceiver 10 may be equipped to utilize a magnetic field communication system, and/or an analog communication system, and/or a digital communication system, such that a single implantable transceiver 10 may communicate with both an old and a new IMD 20 within a patient.

Figure 9:
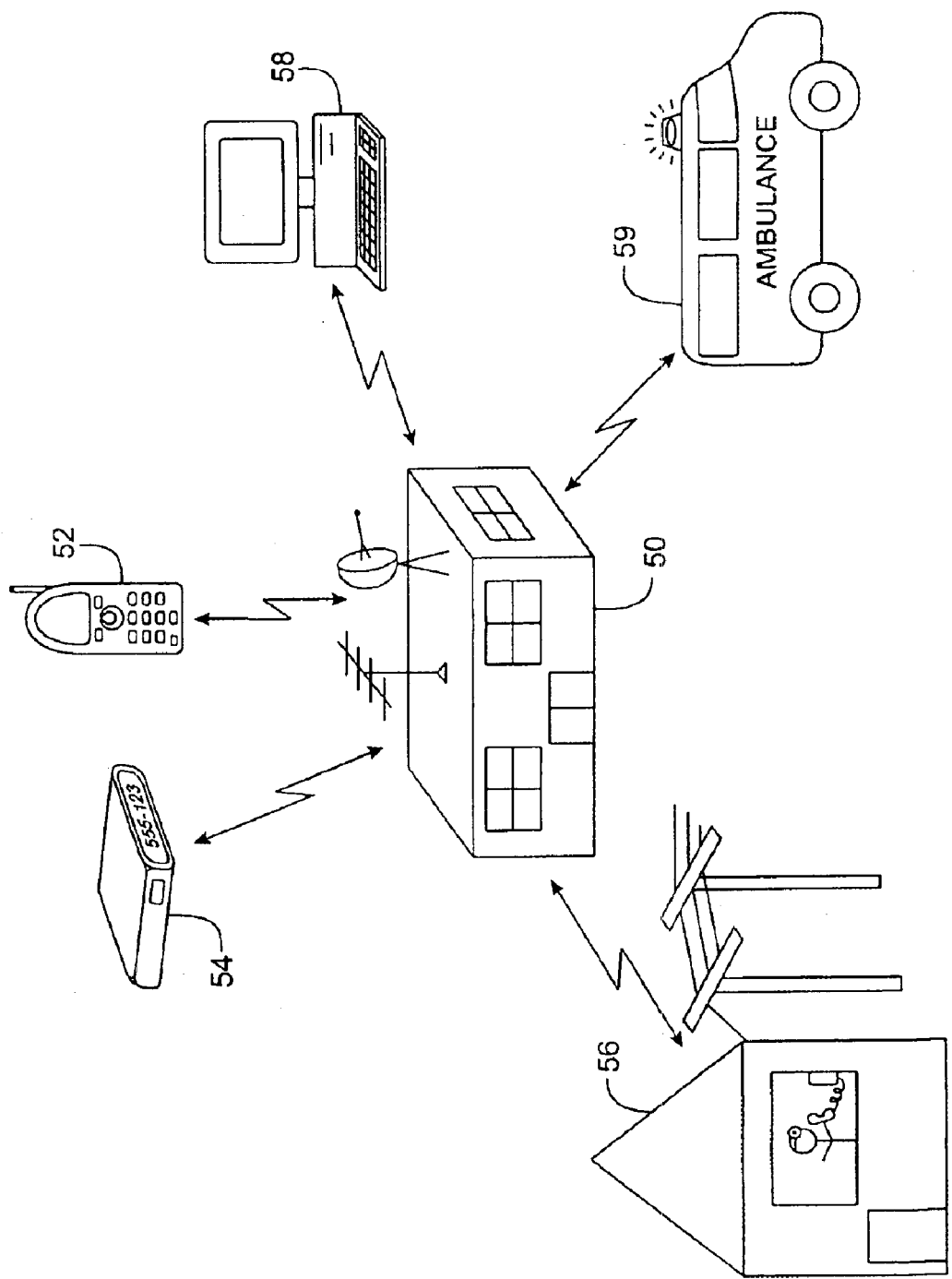
FIG. 9 is a conceptual drawing showing the operation of a monitoring center in communication with various medical personnel communication devices.

FIG. 9 illustrates the monitoring center 50 in communication with various medical personnel response devices. The term medical personnel refers to physicians, nurses, residents, orderlies, or other staff capable of offering the needed medical attention to the patient. A response device is any device capable of receiving and displaying a message to a person, and sending a response that indicates receipt of the message back to the origin of the message. For example, common response devices are personal computers, telephones, and pagers. The above-listed examples of medical personnel and response devices are given only as examples and are not meant to limit the scope of the invention.

In some embodiments of the invention, data received by the monitoring center 50 from the implantable transceiver 10 indicates the patient is in need of immediate medical care. In such a case, the monitoring center 50 contacts an ambulance or medical personnel to provide the necessary care. For example, a physician can be contacted on a wireless or portable telephone 52 or at the physician's home 56 via a land-line telephone network. In other examples, medical personnel can be contacted via e-mail received on a personal computer 58. Other response devices include pagers 54 and radio communication to an ambulance 59. The monitoring center 50 can send an alert message to many medical personnel response devices simultaneously. Alternatively, the monitoring center 50 can send an alert message to a single response device such as the personal computer 58 of an individual physician.

In some embodiments of the invention, the monitoring center 50 uses a database containing medical personnel contact information. The contact information stored in the database can include medical personnel names, positions, schedules, e-mail addresses, telephone and pager numbers, and other information useful in contacting the medical personnel. The medical personnel contact information can be organized within the database in any of a variety of well known ways.

Figure 10:
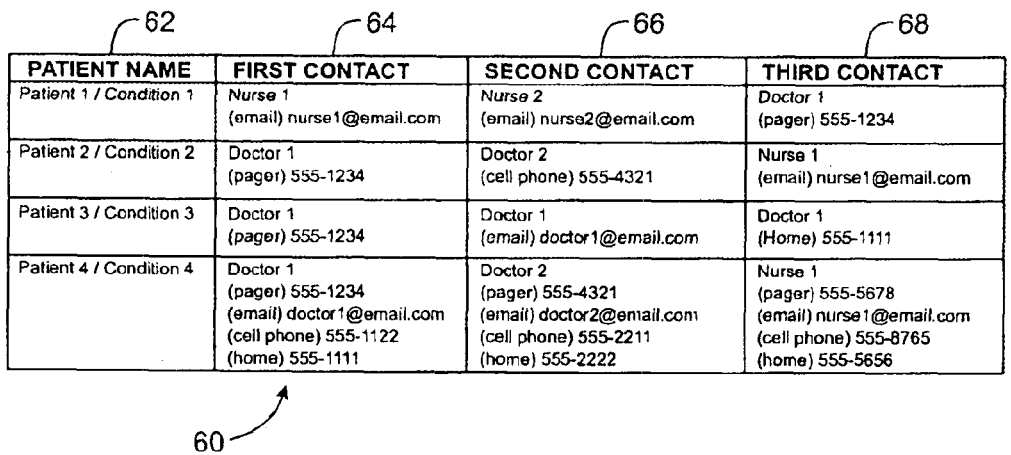
FIG. 10 is a block diagram illustrating a database of medical personnel contact information.

FIG. 10 illustrates one embodiment of a medical personnel contact database 60 for use in the system described herein, wherein the contact information includes data indicating a hierarchy of medical personnel contacts. In some embodiments, the hierarchy can be organized, for example, according to the patient in need or according to the medical condition of the patient (e.g. emergency or non-emergency; life-threatening or non-life-threatening). In this embodiment, the database 60 indicates a first contact and subsequent priority-level contacts to use in response to patient needs. One of skill in the art will recognize that the database can be organized in a variety of ways, and the examples illustrated and discussed herein are not meant to limit the scope of the invention.

For example, referring to FIG. 10, the database 60 contains data representing the patient name and medical condition of the patient represented in column 62. In connection with each patient and/or medical condition, a hierarchy of contact information is provided. Each patient 62 is assigned a first contact indicated in column 64. In addition, each patient is assigned subsequent contacts, such as a second contact indicated in column 66 and a third contact indicated in column 68. In some embodiments, the data base 60 can include more contacts depending on the needs of the patients and the availability of medical personnel.

In one embodiment, if the data received from the implantable transceiver 10 by the monitoring center 50 indicates that Patient 1 needs medical attention, the monitoring center 50 will access the database 60, and retrieve the contact information corresponding to Patient 1. The monitoring center 50 will first attempt to contact a first contact 64 Nurse 1 by sending an alert message to the e-mail address nurse1@email.com. If Nurse 1 does not respond to the alert message after a predetermined amount of time, the monitoring center 50 will send the alert message to a second contact 66 Nurse 2 at the e-mail address nurse2@email.com. If Nurse 2 does not respond after a predetermined period of time, the monitoring center 50 will send the alert message to a third contact 68 Doctor 1 at the pager number 555–1234. The monitoring center 50 will continue to send the alert message to multiple contacts until a message is received by the monitoring center 50 acknowledging receipt of the alert message.

In another example, after receiving data from the implantable transceiver 10 indicating a Patient 4 needs medical attention, the monitoring center 50 sends an alert message to multiple response devices of the first contact 64 Doctor 1. Thus, the monitoring center send the alert message to the pager number 555–1234, the e-mail address doctor1@email.com, the cellular phone number 555–1122, and the home phone number 555–1111. If no response is received from Doctor 1 within a predetermined time period, the monitoring center 50 sends the alert message to the various response devices of a second contact 66 Doctor 3. The monitoring center continues to send the alert message to the response devices of the various contacts in order of priority until a message is received by the monitoring center 50 in response to the alert message.

In some embodiments, the hierarchy of contacts is organized based on the medical condition or need of the patient rather than the identity of the patient. For example, if the monitoring center 50 receives data from the implantable transceiver 10 indicating that a patient needs treatment for Condition 2, the monitoring center will send an alert message to a first contact 64 Doctor 1. The alert message will then be sent to subsequent-priority contacts until a response to the alert message is received by the monitoring center 50.

Figure 11:
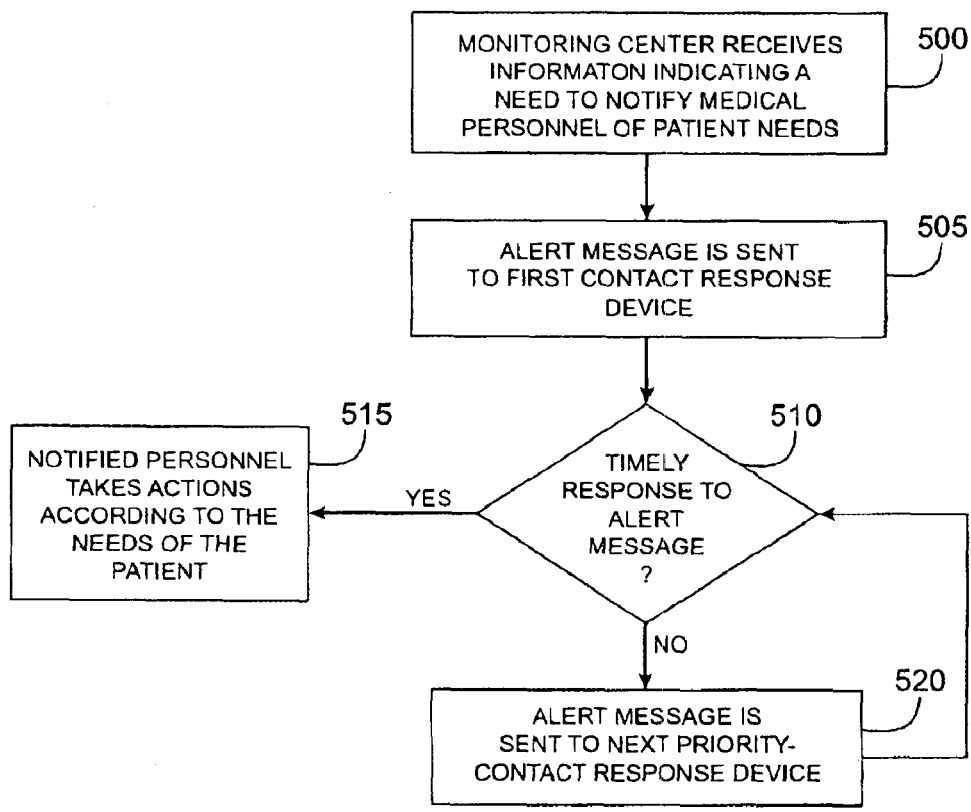
FIG. 11 is a flowchart illustrating a method of notifying medical personnel of a patient's medical condition.

FIG. 11 is a flowchart illustrating the operation of the monitoring center in one embodiment of the invention. In step 500, the monitoring center 50 receives data from the implantable transceiver 10 indicating the IMD patient needs medical attention. Such data can indicate the IMD 20 is not operating properly and needs to be reprogrammed in a timely manner. In other examples, the data indicates an emergency situation wherein the patient needs immediate medical treatment. Moving to step 505, the monitoring center 50 sends an alert message to a first contact response device of one or more medical personnel. In some embodiments, the alert message contains information regarding the patient's name, condition and location, as well as any other information useful in satisfying the needs of the patient. Some examples of response devices is given above with reference to FIG. 10. In addition, some examples of first contact medical personnel are given above with reference to FIG. 10.

Next, in step 510, the monitoring center 50 determines whether there has been a timely response to the alert message. If a response is received within a predetermined amount of time, the process moves to step 515, wherein the medical personnel that received the alert message acts in response to the needs of the patient. For example, the medical personnel can prepare reprogramming instructions for the IMD 20 or dispatch emergency medical personnel to the location of the patient. In some embodiments of step 515, the medical personnel communicates with the monitoring center 50 to obtain information regarding the patient's name, condition and location, as well as any other information useful in satisfying the needs of the patient.

If a response to the alert message is not received within the predetermined time period, the process moves to step 520, wherein the alert message is sent to the next priority contact response device. For example, with reference to FIG. 10, if no response was received from a first contact 64, the alert message is sent to a second contact 66. Similarly, if no response was received from a second contact 66, the alert message is sent to a third contact 68.

Thus, the invention described herein resolves and overcomes the longstanding problem in the art of the inability of transceivers to communicate with older, previously implanted IMDs by providing an implantable transceiver which is electronically independent from the IMD. This problem is also overcome by providing an implantable transceiver with multiple communication systems compatible with old and new IMDs.

The invention described herein fulfills the need to remotely monitor and communicate with an IMD without requiring pre-scheduling or an office visit by providing an implantable transceiver capable of long-range communication with a central monitoring center to facilitate the remote reprogramming of an IMD within a patient. The invention described herein also obviates the need for multiple transceivers or integrated transceivers to communicate with multiple IMDs within a patient by providing an implantable transceiver capable of monitoring and communicating with multiple IMDs while remaining electronically isolated from the IMDs. In this way, surgery time and expense is minimized. Furthermore, the invention provides a transceiver capable of automatically reprogramming and monitoring an IMD without intervention by medical personnel, further minimizing costs and maximizing patient mobility and independence.

The invention described herein provides a more efficient and reliable means for notifying medical personnel of a patient's needs. Thus, the invention fulfills the need for a responsive and reliable notification system when a patient with an IMD is in need of urgent medical assistance.

What is claimed is:

1. A communication apparatus for use in conjunction with one or more devices which are implanted into a living being, comprising:

at least one two-way transceiver for communicating with at least one of an external monitor and the one or more implanted devices, wherein the at least one two-way transceiver is electrically independent of the one or more implanted devices;

a memory device for storing data;

a control module for processing data stored in the memory device and managing communication using the at least one two-way transceiver; and a power supply which is rechargeable, wherein the power supply is recharged using an electromechanical recharging system.

2. A method of monitoring arid reprogramming at least one device implanted within a living being, the method comprising the steps of:

sensing actions performed by the at least one implanted device and physiologic signals from the living being;

compiling information defining the performed actions and physiological signals into a data report;

storing the data report;

analyzing the data report to determine whether the at least one implanted device operates properly; and remotely reprogramming the at least one implanted device if it is determined in the analyzing step that the at least one implanted device is not operating properly.

3. The method of claim 2 wherein the sensing step is performed by a transceiver apparatus capable of two-way communication with the at least one implanted device.

4. The method of claim 3 further comprising the step of sending the data report from the transceiver apparatus to a monitor external to the living being and located in proximity to the transceiver apparatus.

5. The method of claim 4 further comprising the step of sending the data report from the external monitor to a monitoring center via a communication network.

6. A method of monitoring and responding to the physical condition of a patient, wherein the patient has one or more devices implanted in the patient's body, comprising the steps of:

sensing actions performed by the one or more implanted devices and physiologic signals from the patient;

compiling information defining the performed actions and physiological signals into a data report;

storing the data report;

analyzing the data report to determine whether the at least one implanted device operates properly and whether the patient needs medical treatment;

notifying medical personnel if it is determined that the implanted device in not operating properly; and alerting medical personnel if it is determined that the patient needs medical treatment.

7. A system for notifying medical personnel of a patient's medical needs, wherein the patient has at least one device implanted in the patient's body, comprising:

a monitor located external to the patient's body;

a transceiver located so as to transmit and receive signals between the transceiver and the implanted device, and so as to transmit and receive signals between the transceiver and the monitor such that device operation information is communicated from the implanted device via the transceiver to the monitor, and such that control signals are communicated from the monitor via the transceiver to the implanted device; and a monitoring center configured so as to receive the device operation information from the monitor, and so as to notify a first contact medical personnel that the patient needs medical treatment, and so as to notify a second medical personnel that the patient needs treatment if the first contact medical personnel does not respond to notification, and so as to notify subsequent contact medical personnel if previous contact medical personnel do not respond to notification.

8. A method of notifying medical personnel of a patient's medical needs, wherein the patient has at least one device implanted in the patient's body, comprising the steps of:

determining that the patient needs medical treatment;

sending an alert message to a medical contact; and sending a subsequent alert message to a subsequent medical contact if a response message in response to a previously sent alert message is not received.

9. A system for monitoring and reprogramming at least one device implanted within a living being comprising:

means for sensing actions performed by the at least one implanted device and physiologic signals from the living being;

means for compiling information defining the performed actions and physiological signals into a data report;

means for storing the data report;

means for analyzing the data report to determine whether the at least one implanted device operates properly; and means for remotely reprogramming the at least one implanted device if it is determined by the analyzing means that the at least one implanted device is not operating properly.

10. The system of claim 9 wherein the sensing means is a transceiver apparatus capable of two-way communication with the at least one implanted device.

11. The system of claim 10 further comprising means for sending the data report from the transceiver apparatus to a monitor external to the living being and located in proximity to the transceiver apparatus.

12. The system of claim 11 further comprising means for sending the data report from the external monitor to a monitoring center via a communication network.

13. A system for monitoring and responding to the physical condition of a patient, wherein the patient has one or more devices implanted in the patient's body, comprising:

means for sensing actions performed by the one or more implanted devices and physiologic signals from the patient;

means for compiling information defining the performed actions and physiological signals into a data report;

means for storing the data report;

means for analyzing the data report to determine whether the at least one implanted device operates properly and whether the patient needs medical treatment;

means for notifying medical personnel if it is determined that the implanted device is not operating properly; and means for alerting medical personnel if it is determined that the patient needs medical treatment.

14. A system for notifying medical personnel of a patient's medical needs, wherein the patient has at least one device implanted in the patient's body, comprising: means for determining that the patient needs medical treatment;

means for sending an alert message to a medical contact; and means for sending a subsequent alert message to a subsequent medical contact if a response message in response to a previously sent alert message is not received.

15. A method of monitoring and reprogramming at least one device implanted within a living being, the method comprising the steps of:

sensing actions performed by the at least one implanted device and physiologic signals from the living being;

evaluating the sensed actions and physiological signals to determine the operation integrity of the at least one implanted device; and remotely reprogramming the at least one implanted device if it is determined that the at least one implanted device is not operating properly.

16. The method of claim 15 wherein the sensing step is performed by a transceiver apparatus capable of two-way communication with the at least one implanted device.

17. The method of claim 16 further comprising the step of sending the data report from the transceiver apparatus to a monitor external to the living being and located in proximity to the transceiver apparatus.

18. The method of claim 17 further comprising the step of sending the data report from the external monitor to a monitoring center via a communication network.

19. A system for monitoring and reprogramming at least one device implanted within a living being, the system comprising:

means for sensing actions performed by the at least one implanted device and physiologic signals from the living being;

means for evaluating the sensed actions and physiological signals to determine the operation integrity of the at least one implanted device; and means for remotely reprogramming the at least one implanted device if it is determined that the at least one implanted device is not operating properly.

* * * * *